(12) United States Patent
Goldstein et al.

(10) Patent No.: US 10,954,484 B2
(45) Date of Patent: Mar. 23, 2021

(54) AUTOMATED BIOLOGICAL SAMPLE COLLECTION SYSTEM AND METHODS

(71) Applicant: INNOVO MIMETICS LIMITED, Jerusalem (IL)

(72) Inventors: Robert Goldstein, Tel Yosef (IL); Jonathan Goldstein, Jerusalem (IL); Avner Yeffet, Mevasseret Zion (IL); Julia Rifman, Modiin (IL); Renana Hajbi, Maskeret Batya (IL); Leah Blum, Jerusalem (IL)

(73) Assignee: INNOVO MIMETICS LIMTED, Jerusalem (IL)

( * ) Notice: Subject to any disclaimer, the term of this patent is extended or adjusted under 35 U.S.C. 154(b) by 0 days.

(21) Appl. No.: 16/541,182

(22) Filed: Aug. 15, 2019

(65) Prior Publication Data
US 2020/0140804 A1    May 7, 2020

Related U.S. Application Data

(63) Continuation of application No. 15/158,617, filed on May 19, 2016, now Pat. No. 10,421,940, which is a continuation-in-part of application No. 13/017,011, filed on Jan. 30, 2011, now abandoned.

(60) Provisional application No. 61/300,071, filed on Feb. 1, 2010.

(51) Int. Cl.
*A61B 17/32* (2006.01)
*C12M 1/36* (2006.01)
*C12M 1/26* (2006.01)
*C12M 3/00* (2006.01)
*C12M 1/00* (2006.01)

(52) U.S. Cl.
CPC ............ *C12M 41/48* (2013.01); *C12M 21/06* (2013.01); *C12M 33/04* (2013.01); *A61B 17/32* (2013.01); *C12M 41/14* (2013.01)

(58) Field of Classification Search
None
See application file for complete search history.

(56) References Cited

U.S. PATENT DOCUMENTS 7,249,569 B2 * 7/2007 Mendu ................. A01K 45/007
119/6.8

* cited by examiner

*Primary Examiner* — Benjamin P Blumel
(74) *Attorney, Agent, or Firm* — Daniel J. Swirsky; AlphaPatent Associates Ltd.

(57) ABSTRACT

An egg sealing unit for an automated biological sample collection system and method of use. The egg sealing unit seals the section of egg from which the shell has been removed. The egg sealing unit includes a sampler, an applicator and an imaging adaptor providing an optical conduit between the surface of an egg and the CAM. The applicator is configured to deliver exogenous material to the CAM, the sampler is configured to collect samples from the CAM and the imaging adaptor allows the CAM to be monitored.

12 Claims, 18 Drawing Sheets

AUTOMATED BIOLOGICAL SAMPLE COLLECTION SYSTEM AND METHODS

CROSS-REFERENCE TO RELATED APPLICATIONS

This application is a Continuation of U.S. patent application Ser. No. 15/158,617, filed May 19, 2016, which is itself a Continuation-In-Part of U.S. patent application Ser. No. 13/017,011, filed Jan. 30, 2011, which claims the benefit of priority from U.S. Provisional Patent Application No. 61/300,071, filed Feb. 1, 2010. The contents of the above-referenced applications are incorporated herein by reference in their entirety.

FIELD OF THE INVENTION

The embodiments disclosed herein relate to an automated sample collection system and method. In particular a system is disclosed for performing assays on fertilized and embryonated eggs.

BACKGROUND OF THE INVENTION

The embryonic chick has been used as an in vivo model for the investigation of a number of biological systems for over a century. It is noted for its simplicity, availability, immune-deficient properties, and for the highly vascularized structure of the Chorioallantoic Membrane (CAM).

Many in vivo systems, particularly model systems for studying human tissues and organs, require transplanting an examined graft into an immune compromised animal, in order to avoid graft rejection. Such animals, for example, Severe Combined Immune Deficient (SCID) mice, are expensive, sickly and hard to maintain.

The avian egg provides a low cost and readily available alternative to in vivo testing upon sentient animals. The avian egg has been used in growth of viruses for vaccine generation, angiogenesis assays, teratogenicity testing, tumor cells and the like.

Such assays may be performed on the embryos, or on microbes, cells and tissues grafted, injected or applied to fertilized avian eggs. For example, the Hen's Egg Test-Chorioallantoic Membrane (HET-CAM) assay is a well-known method for screening the irritancy potential of topically applied compositions such as cosmetics.

However, such procedures are generally performed manually, are labor intensive and are not practical on the large scale. Furthermore, because there is human intervention when handling the eggs as well as in the sampling and analysis of the assays, these procedures are not easily repeatable. It is therefore difficult to produce large numbers of identical eggs and assays to be used for statistical analysis.

It will be appreciated, therefore, that there is a need for an automated process for producing biotechnological assays. The system and method described herein address this need.

SUMMARY OF THE INVENTION

Embodiments described herein disclose a biological sample collection system. The system comprises at least one incubator, configured to control the environment of at least one egg; at least one applicator, configured to deliver exogenous material to the at least one egg; and at least one sampler, configured to collect samples from the at least one egg. Typically, the egg comprises a fertilized avian egg. Optionally, the at least one egg comprises a chimeric system.

Embodiments described herein disclose a method for use in an automated sample collection system for collecting a set of biological samples from at least one fertilized egg, the system comprises: at least one incubator configured to control the environment of the at least one fertilized egg; a shell removal apparatus configured to remove at least a section of the shell providing access to a chorioallantroic membrane (CAM) of the at least one fertilized egg; at least one applicator configured to deliver exogenous material to the fertilized egg; at least one sampler configured to collect samples from the at least one fertilized egg; and at least one controller unit, the method for operating the sample collection system such that the associated process of collecting the samples is performed in an improved manner, the method comprising the steps:

configuring, by the controller unit, the automated sample collection system according to at least one automated setup parameter;

pricking, by the shell removal apparatus, the chorioallantroic membrane (CAM) of the at least one fertilized egg;

delivering, by the at least one applicator, at least one exogenous material to the at least one fertilized egg using at least one delivery mechanism associated with the at least one sampler;

incubating, by the at least one incubator, the at least one fertilized egg for a period of incubation; and harvesting, by the at least one sampler, at least one sample from the at least one fertilized egg.

The step of pricking the chorioallantroic membrane (CAM) of the at least one fertilized egg, comprises: removing at least a part of the shell of the at least one fertilized egg at the widest side comprising an air pocket; and exposing at least a part of the chorioallantoic membrane (CAM).

Where appropriate, the step of pricking, further comprises: placing a tube into the chorioallantoic membrane (CAM).

The step of delivering at least one exogenous material comprises engrafting, by at least one delivery mechanism, a population of cells to said at least one fertilized egg.

Where appropriate, the step of delivering at least one exogenous material, comprises injecting, by at least one delivery mechanism, at least one exogenous material into a designated blood vessel of at least one fertilized egg.

The step of injecting at least one exogenous material, comprises: directing the injection into the designated blood vessel in the direction of blood flow.

Where required, the method may further comprise: determining the direction of blood flow in the designated blood vessel.

Where required, the method may further comprise: selecting the designated blood vessel having a known direction of blood flow.

As appropriate, the step of determining the direction of blood flow in the designated blood vessel comprises: using a flow-detector to determine the blood flow direction of the designated blood vessel.

As appropriate, the step of determining the direction of blood flow in the designated blood vessel, comprises: using image processing technique configured to determine the direction of blood flow according to the shape of the designated blood vessel.

As appropriate, the step of directing the injection into the designated blood vessel in the direction of blood flow comprises: identifying an umbilical vein connecting the chorioallantoic membrane (CAM) and an embryo of the at least one fertilized egg, and injecting the exogenous material into the umbilical vein in a direction from the chorioallantoic membrane (CAM) to the embryo.

As appropriate, the step of injecting at least one exogenous material comprises: using the at least one delivery mechanism comprising a 30 gauge needle.

Variously, the at least one exogenous material is selected from at least one of a group consisting of: cells, tumor cells, bacteria, viruses, chemicals, drugs, skin explants and external modulators.

As appropriate, the period of incubation is selected to be sufficient to allow engraftment of the population of cells to the chorioallantoic membrane (CAM) of the at least one fertilized egg.

Optionally, the step of injecting at least one exogenous material is configured to keep the at least one delivery mechanism in the designated blood vessel for 10 seconds.

Optionally, the step of injecting at least one exogenous material is configured to apply surgical glue when the at least one delivery mechanism is withdrawn from the designated blood vessel.

Variously, the at least one delivery mechanism comprises at least one of a group consisting of: syringes, needles, angled needles, jacketed needles, cantilevered needles, pipettes, multichannel pipettes, tweezers, tubing, magnetic droppers and combinations thereof.

The step of engrafting at least one exogenous material comprises: identifying a junction between a first blood vessel and a second blood vessel on the chorioallantroic membrane (CAM), and engrafting said population of cells at the junction.

Variously, the step of configuring the automated sample collection system, comprises defining a configuration parameter selected from a group consisting of a harvesting date and time; an engrafting date and time; an injecting date and time; an identified peak time for harvesting; a sample cell extracting days and combinations thereof.

Where required, the method may further comprise analyzing, by at least one imaging unit, the chorioallantoic membrane (CAM) and the embryo at a pre-configured period of time.

Where required, the method may further comprise using, by the at least one sampler, invasive techniques to collect samples from the at least one fertilized egg.

Variously, the step of analyzing comprises: using, by the at least one imaging unit, a non-invasive photographic technique selected from a group consisting of an imaging fluorescence-based photography technique; an imaging luminescence-based photography technique; an imaging conventional illumination-based photography technique; an imaging ultrasonic-based technique; an imaging X-ray based technique; a heat detector based technique; radioactivity detector based technique; MRI-based technique; and combinations thereof.

Where required, the method may further comprise: using a high-resolution imaging fluorescence-based photography technique; marking each cell to be individually identifiable; and indicating an associated cell type by expressing additional fluorescent labels.

As appropriate, the step of analyzing comprises testing, by the at least one imaging unit, the convergence of blood vessels towards the graft.

As appropriate, the step of analyzing comprises: testing, by the at least one imaging unit, for variations in the distribution of density of chorioallantoic membrane (CAM) blood vessels next to the site of the graft.

As appropriate, the step of analyzing, comprises: mapping, by the at least one imaging unit, of blood vessels branching.

Where required, the method may further comprise at least one of: analyzing growth of viruses for generation and testing/development of vaccines; analyzing of chemotherapies on human or mammalian cancer cells transplanted to an egg; analyzing for angiogenic properties of substances applied to the chorioallantoic membrane (CAM); analyzing of toxicity to the embryo (teratogenicity) or transplanted human or mammalian skin transplanted to the CAM including irritation and sensitization.

Where required, the method may further comprise monitoring at least one activity selected from the group consisting of: the absorption of the bolus; blood leakage from the blood vessels; bolus ejected from the at least one fertilized egg; and combinations thereof.

In some embodiments of the current disclosure, an automated biological sample collection system is disclosed for collecting biological samples from at least one fertilized egg, the system comprising a set of system components: at least one incubator configured to control the incubating environment of at least one egg; at least one applicator comprising at least one delivery mechanism configured to deliver exogenous material to at least one egg; at least one sampler configured to collect at least one sample from at least one egg; at least one egg supporting apparatus configured to accommodate at least one egg; a shell removal apparatus configured to remove at least a section of the shell providing access to the chorioallantroic membrane (CAM); at least one imaging device operable to provide monitoring of system components; and at least one controller unit operable to communicate with at least one system component and drive the system in an automatic manner.

Variously, at least one controller unit is operable to control at least one factor selected from: incubation conditions, incubation periods, calculation of incubation periods, selection of incubation periods, transfer of eggs from the incubator to the applicator, transfer of eggs from the incubator to the sampler, applicator control, detection of non-viable eggs, removal of non-viable eggs, image analysis, coordination of feedback from system components, shell removal, sampler activation, data collection, system configuration and combinations thereof.

Variously, the system further comprising at least one feedback mechanism selected from a group consisting of: video sensors, light sensors, sonar, shadow contrast detectors, interferometers, piezoelectric elements, a tuning fork and combinations thereof.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects of the invention. In this regard, no attempt is made to show structural details in more detail than is necessary for a fundamental understanding; the description taken with the drawings making apparent to those skilled in the art how the several selected embodiments may be put into practice. In the accompanying drawings.

DETAILED DESCRIPTION

Figure 1A:
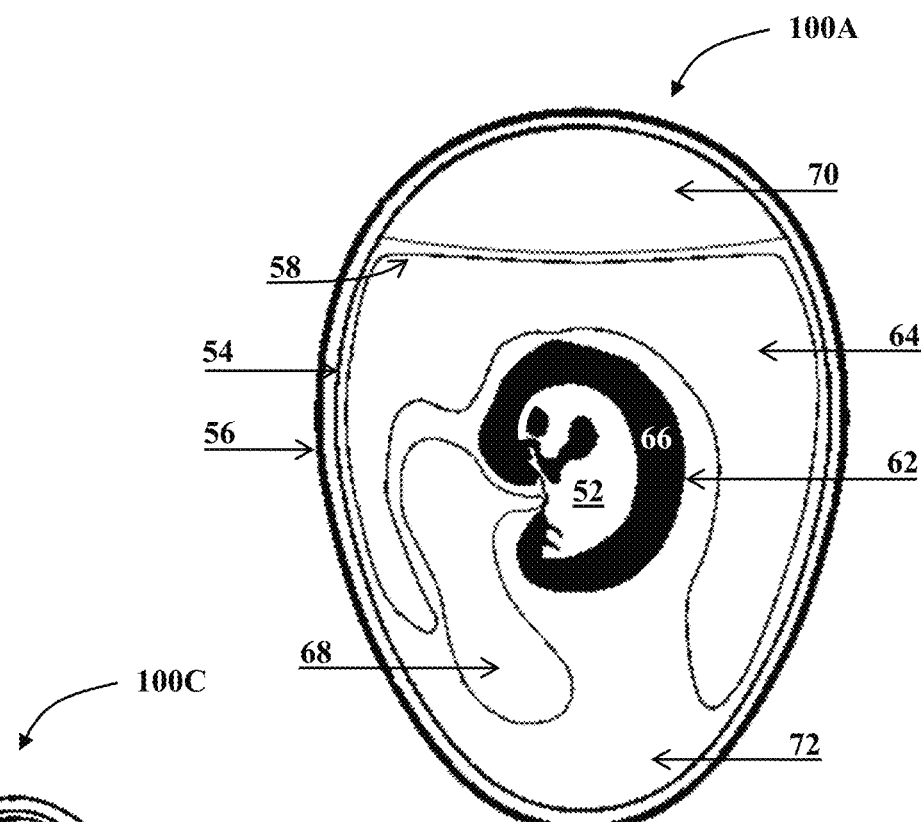
FIG. 1A is a schematic diagram representation of an embryonated chicken egg structure.

The microcirculation within the chorioallantoic membrane (CAM) of the chick is particularly well suited for in vivo observation and has been used extensively as an assay to detect angiogenic activity.

Aspects of the present disclosure relate to system and methods of an automated biological sample collection system using an automated process for producing biotechnological assays on fertilized and embryonated eggs.

The embryonated egg is a complex structure and is particularly well suited for in vivo observation, utilized as a laboratory host system for virus research, commercial production of vaccines, detecting angiogenic activity, special investigations and the like. The embryonated egg is comprised of a developing embryo and several supporting membranes (chorioallantoic, amniotic, yolk), which enclose cavities or "sacs" within the egg. The developing embryo and its membranes provide the diversity of cell types that are needed for successful replication of a wide variety of different viruses, for example. The chorioallantoic membrane (CAM) is the largest of the embryo membranes enclosing the largest cavity within the egg, the allantoic cavity. The amniotic membrane encloses the embryo and forms the amniotic cavity of the embryonated chicken egg. The yolk sac is attached to the embryo and contains the nutrient that the embryo utilizes during embryonic development and the immediate post-hatch period.

The automated biological sample collection system comprises an incubator configured to control the incubating environment of at least one egg; an applicator comprising at least one delivery mechanism configured to deliver exogenous material to a chorioallantroic membrane (CAM) of the at least one egg; a sampler configured to collect samples from the at least one egg, invasively or non-invasively; at least one imaging device operable to provide monitoring of system components; and at least one controller unit operable to communicate with at least one system component and drive the system automatically.

Description of the Embodiments

In various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard-disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting.

The Embryonated Egg:

Reference is now made to FIG. 1A, there is provided an embryonated egg structure diagram, which is generally indicated at 100A, illustrating the structure of an embryonated egg.

The embryonated egg 100A comprises a developing embryo 52, a shell membrane 54 (the chorion) is the outermost membrane and lines the inside of the egg outer shell 56; and additional supporting membranes: a chorioallantoic membrane (CAM) 58, an amniotic membrane 60, a yolk membrane 62, which enclose cavities or "sacs" within the embryonated egg. The chorioallantoic membrane (CAM) 58 is the largest of the embryo membranes enclosing the largest cavity within the egg, the allantoic cavity 64. The amniotic membrane 60 encloses the developing embryo 52 and forms the amniotic cavity 66 around the developing embryo 52. The yolk membrane 62 encloses the yolk sac 68 which is attached to the developing embryo 52.

The embryonated egg 100A further comprises an air pocket 70 which is the space at the rounded end and has a function in respiration and pressure adjustments. Additionally, the embryonated egg 100A comprises albumin 72, which is the egg white and consists mainly of protein.

It is noted that allantoic cavity 64, formed by the chorioallantoic membrane (CAM) 58, within an egg is a membranous sac which is involved in gas exchange, storage of wastes and absorption of nutrients for the developing chick embryo 52; the amniotic cavity 66 is filled with liquid and serves to protect the developing embryo 52 against physical damage and is also functioning as an area of exchange of molecules. The amniotic membrane 60 is the innermost membrane which encloses the developing embryo to provide a protective environment to the developing embryo 52 of the embryonated chicken egg.

Figure 1C:
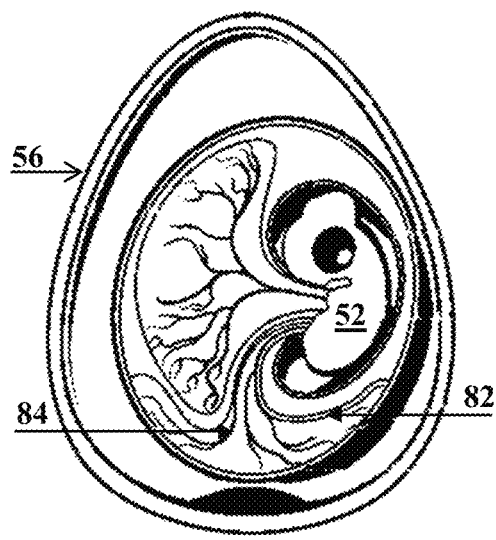
FIG. 1C is a schematic diagram representation of the blood vessel structure including the umbilical vein and the umbilical artery of an embryonated chicken egg.
Figure 1B:
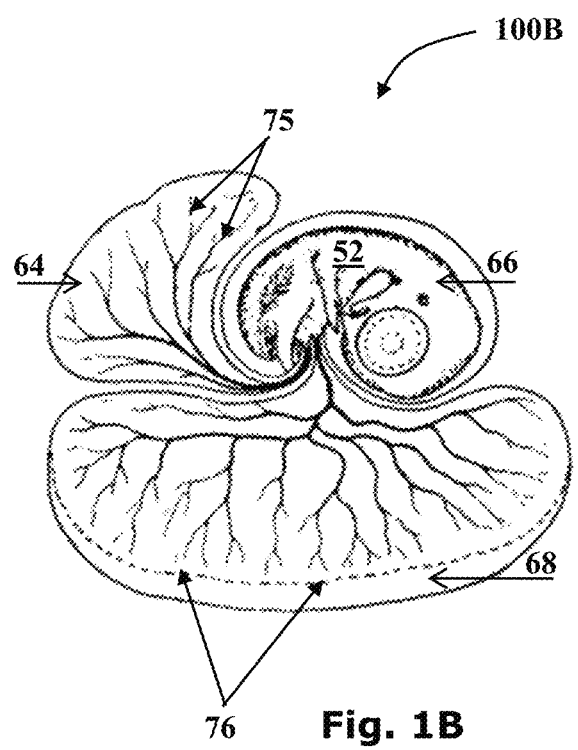
FIG. 1B is a schematic diagram representation of the blood vessel structure of the chorioallantoic membrane (CAM) of an embryonated chicken egg.

Reference is now made to FIG. 1B, there is provided a blood vessel structure diagram, which is generally indicated at 100B, illustrating a blood vessel structure of the chorioallantoic membrane (CAM) of an embryonated chicken egg.

The blood vessel structure diagram 100B illustrates the formation of a supportive matrix for the extensive vascular network that crosses through the chorioallantoic membrane (CAM) growing during incubation. The diagram 100B is illustrating a branching network of large and small blood vessels over the major cavities ("sacs") within the embryonated egg: the allantoic cavity 64 includes the allantoic blood vessels branching 75, the amniotic cavity 66 around the developing embroy 52 and the yolk sac 68 which includes the vitelline blood vessel branching 76. As appropriate, the vitelline arteries are the arterial counterpart to the vitelline veins. Like the veins, they play an important role in the vitelline circulation of blood to and from the yolk sac 68.

It is noted that the chorioallantoic membrane (CAM) develops in a short time from a small vascular membrane into a structure that covers the entire inner surface of the shell displaying a densely organized vascular network. The blood vessel network includes veins which are responsible for transporting blood throughout the body, arteries and capillaries that carry blood away from the body and exchange nutrients, waste, and oxygen. Further, closest to the developing embryo 52 is the primary stratum which is the thickest part of the chorioallantoic membrane (CAM), approximately 20 to 100 micrometer thick, and the largest chorioallantoic membrane (CAM) vessels (up to approximately 1 mm in diameter) run immediately underneath and are anchored to this layer via thin, perivascular sheathes. Smaller vessels (less than 200 micrometer diameter) are embedded within the main layer. Immediately external to the primary layer of chorioallantoic membrane (CAM) is a capillary plexus, or blood sinus. Above this sinus lies a thin stratum (approximately 1 micrometer) that is composed of four sublayers originally derived from the chorion (basement membrane, epithelial cell layer, peptidoglycan extracellular matrix, and basal lamina).

Accordingly, the identification of the various blood vessel (veins, arteries, capillaries) may be useful for the process of injecting exogeneous material, as part of an assay, as elaborated in sections hereinafter.

Reference is now made to FIG. 1C, there is provided another view of the blood vessel structure diagram, which is generally indicated at 100B, illustrating additionally the umbilical vein and the umbilical artery of an embryonated chicken egg.

The view 100C of the blood vessel structure of an embryonated chicken egg includes the egg shell 56 protecting the embryo 52 and illustrates specifically the umbilical vein 82 and the umbilical artery 84 of the embryonated egg.

The Automated System:

The automated biological sample collection system is operable to conduct biological assays, using embryonated eggs, according to a pre-configured specification and carry out the assay schedule automatically. The automation of the biological sample collection system includes automatic mechanical operation controllable via a system controller and further configured to analyze the collected samples automatically using various system components and software techniques. The system is operable to perform clinical assays as well as providing answers to the pharma industry.

Figure 2A:
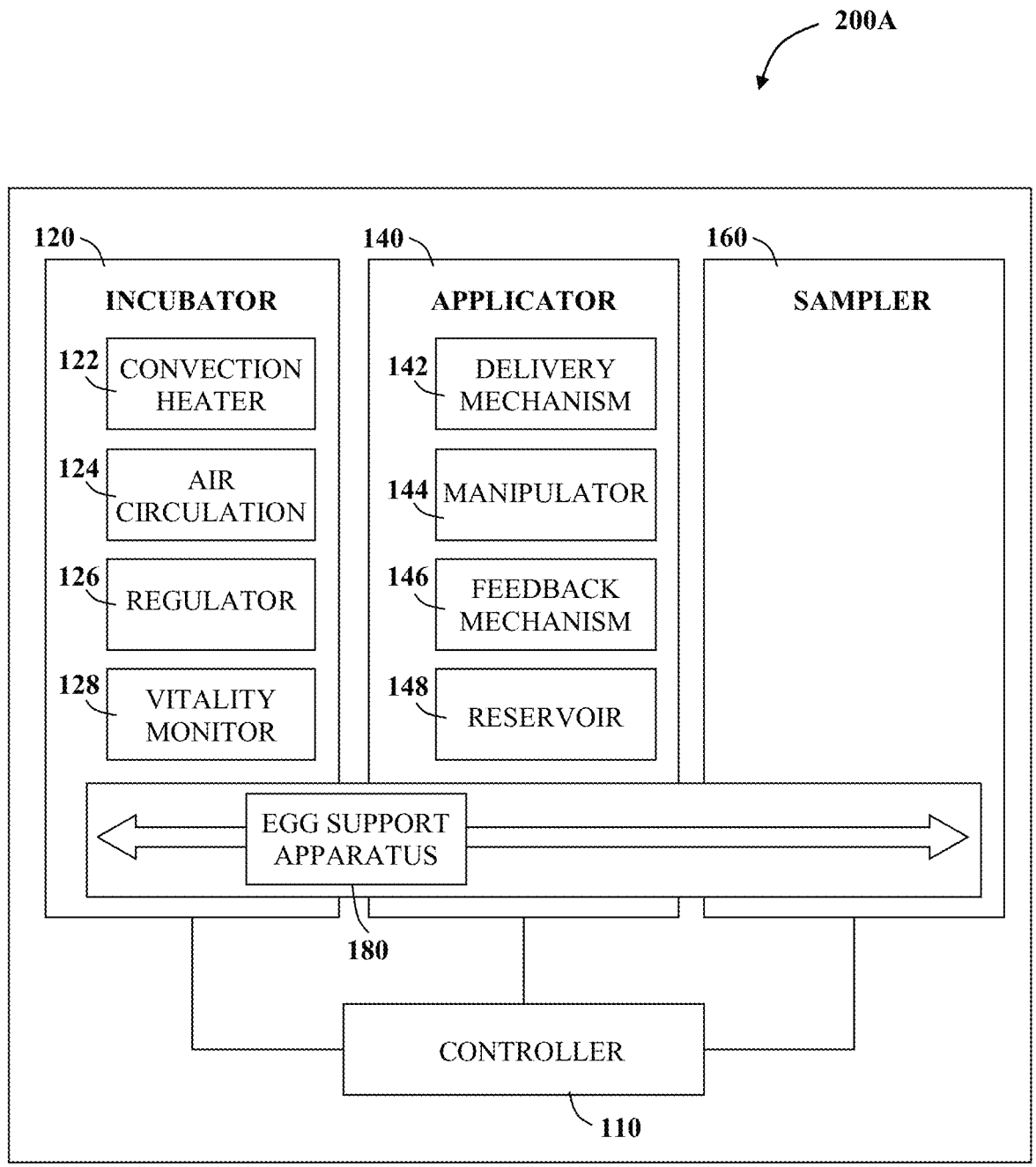
FIG. 2A is a block diagram showing the main elements of an automated biological sample collection system.

Reference is now made to FIG. 2A, there is provided an exemplified block diagram of an automated biological sample collection system, which is generally indicated at 200A, for performing assays on fertilized or embryonated eggs. The automatic sample collection system block diagram 200A represents the main elements of one system embodiment and includes an incubator 120 for incubating an egg, an applicator 140 for applying exogenous material to the egg, a sampler 160 for collecting biological samples from the egg (an egg sealing unit, see FIG. 10) an egg support apparatus 180 and a controller 110 operable to coordinate the system.

It is a feature of the embodiment of the biological sample collection system 200A that it may be used to automate biological screening, particularly of fertilized avian eggs. Consequently, the system 200A may increase the throughput of biotechnological sampling thereby enabling large scale performance of biotechnological assays.

A biological sample collection system 200A of the type disclosed herein may be usefully applied to a variety of technologies. For example, the rapid sampling may make it practical to grow viruses in avian eggs which are harvested to generate vaccines.

In other applications, human or mammalian cancer cells may be transplanted to eggs. These chimeric systems may be used to perform assays of treatments such as chemotherapies, radiotherapies and the like. This technique may be used for drug development applications, for personalized medicine or the like.

Assays may be performed upon various microbes, cells, tissues, organ sections or the like. These may be injected into, grafted upon or otherwise applied to the embryo or fertilized egg. It is particularly noted that assays may be performed upon the chick embryos or upon the chorioallantoic membrane (CAM) of the eggs.

Alternatively, or additionally, assays may be performed for angiogenic properties of substances applied to the chorioallantoic membrane (CAM) or for toxicity to the embryo (teratogenicity) or human or mammalian tissues transplanted to the chorioallantoic membrane (CAM). Such assays may be used to examine irritation, sensitization and the like.

Still further applications will occur to the skilled practitioner.

Figure 2B:
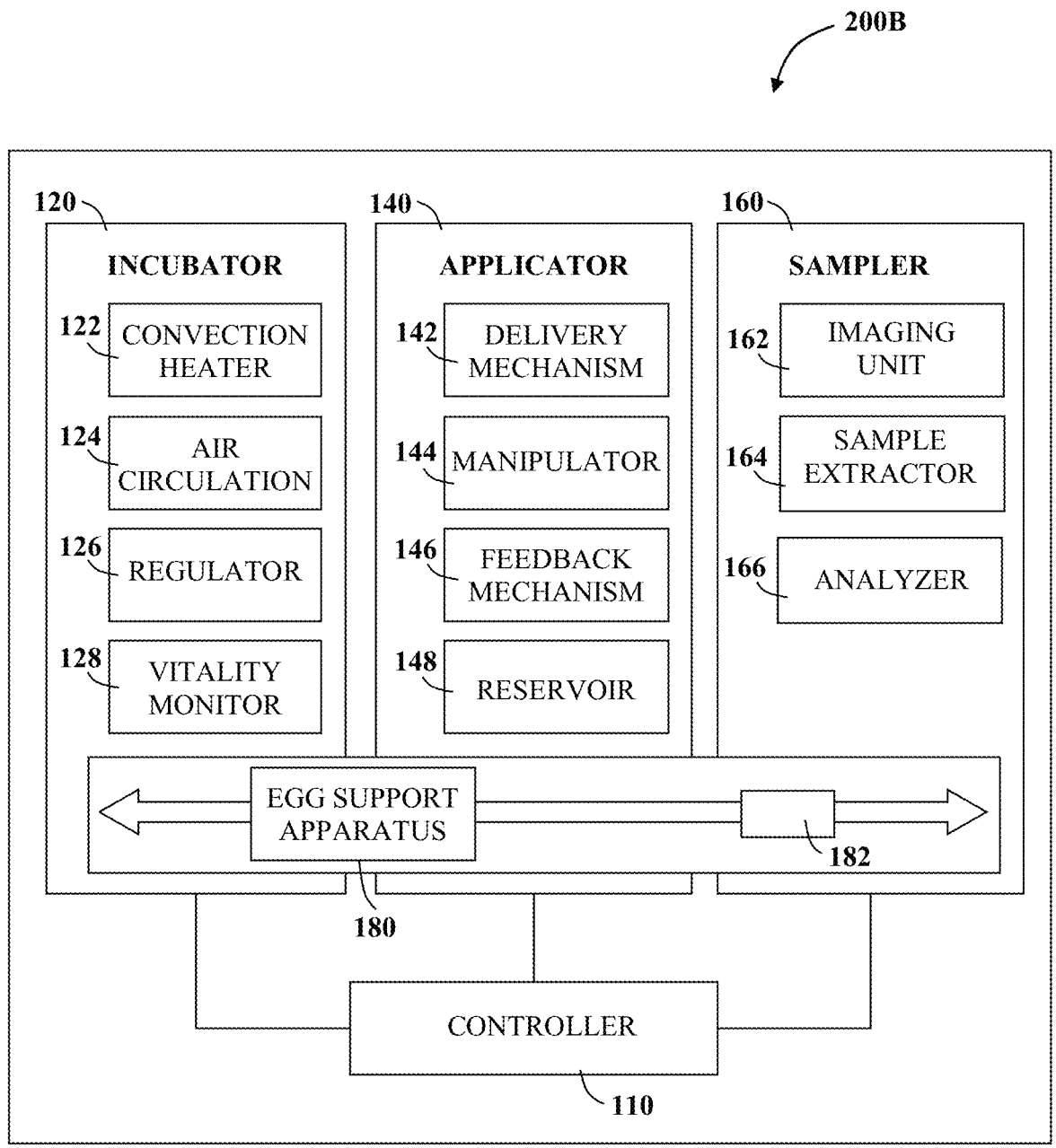
FIG. 2B is a block diagram showing the main elements of another automated biological sample collection system.

Reference is now made to FIG. 2B, there is provided another exemplified block diagram of an automatic biological sample collection system, which is generally indicated at 200B, for performing assays on fertilized or embryonated eggs. The automatic sample collection system block diagram 200B represents the main elements of another system embodiment and includes an incubator 120 for incubating an egg, an applicator 140 for applying exogenous material to the egg, a sampler 160 for collecting biological samples from the egg, an egg support apparatus 180 driven by a driver unit 182 and a controller 110 operable to coordinate the system. As appropriate, the sampler 160 includes an imaging unit 162, a sample extractor 164 and a sample analyzer 166, as detailed in the "The SAMPLER" section.

It is noted that the imaging unit 162 associated with the sampler 160 is presented by example only. Additional imaging devices may be associated with other system elements such as with the applicator 140, egg sealing unit (see FIG. 10) and the incubator 120 to provide better automated tools for performing the assays' analysis.

The Incubator:

The incubator 120 of the automatic biological sample collector system 200A (FIG. 2A) is configured to control the environmental conditions of the eggs. Typically, the incubator 120 maintains environmental conditions selected to support the viability of the fertilized eggs. Furthermore, the incubator may be adapted to control various environmental parameters such as ambient temperature, humidity, air circulation, anti-microbial agent content, ambient pH, egg-turning, pressure, gaseous composition, oxygen content and the like. In eggs where the blood vessels are poorly developed on the CAM, for example following prolonged incubation at low temperatures that halt embryonic development (e.g., 14-20 Celsius), a decrease or increase in air oxygen levels at the CAM surface may induce more robust blood vessel development. Oxygenated air (for example 15-35% oxygen) may be introduced directly to the CAM via the prick hole in the egg using an aspirating needle, for example, or by altering oxygen levels in the entire incubator. The incubator may include a convection heater 122, a water reservoir, for maintaining humidity, an air circulation system 124 such as a fan, as well as regulators 126 operable to maintain conditions within selected ranges. It is further noted that the egg support apparatus 180 may be adapted to turn the eggs during incubation, for example, by tilting a tray repeatedly to simulate the motion of an egg incubated in a natural environment.

The automated biological sample collection system 200A (FIG. 2A) may be adapted to a variety of types of eggs. Typically, chicken, turkey, ostrich, quail, duck, pheasant, grouse, or other bird eggs may be used. It is noted that while the incubation period for chick eggs is 21 days, turkey eggs have longer incubation periods of 28 days while ducks may have incubation periods of up to 42 days depending on the species. Thus the species of the host eggs may be selected to suit requirements, for example such that implanted cells are maintainable for longer.

In various embodiments, the automated biological sample collection system 200A (FIG. 2A) may be used to collect samples from modified avian eggs wherein at least a portion of the egg shell has been removed from the fertilized avian egg. In these embodiments, the egg support apparatus 180 typically includes receptacles adapted for holding at least partially shell-less fertilized eggs. A number of references describe well-known protocols for incubating shell-less, fertilized avian eggs (Hamamichi and Nishigori 2001. Toxicol. Lett. 119: 95-102; Fisher, C. J. 1993. Chick Embryos in Shell-less Culture, Pages 105-115, in Tested studies for laboratory teaching, Volume 5 (C. A. Goldman, P. L. Hauta, M. A. O'Donnell, S. E. Andrews, and R. van der Heiden, Editors). Proceedings of the 5th Workshop/Conference of the Association for Biology Laboratory Education (ABLE); Tufan et al 2004. Akdogan Esat Adiguzel Neuroanatomy, 2004, 3 8-11). Particular reference is made to United States patent application publication number US 2009/0064349, which is incorporated herein by reference. US 2009/0064349 discloses various methods of cultivating transplanted skin explants onto the chorioallantoic membrane (CAM) of fertilized avian eggs. None of these references disclose, or suggest, an automated process for sample collection.

The ambient temperature of incubation is typically within the range of 30 to 40 degrees Celsius such that viable embryos may be maintained. The selected temperature may depend upon other requirements, for example, without wishing to be limited to any particular theory, it is particularly noted that for various applications a temperature of 40 degrees Celsius may be used to increase the effectiveness of chemical inhibitors of tumor growth while supporting the viability of the host embryo (Taylor and Williams, Biochemistry vol. 42, 1956 pp. 57-60).

According to various embodiments, a plurality of incubators may be provided, or a plurality of compartments within an incubator, such that various eggs may be subjected to different environmental conditions during incubation. Additionally or alternatively, the incubator may be adapted to provide gradual variation of environmental conditions, the effects of which may be tested.

In some embodiments, a vitality monitor 128 may be provided which is operable to monitor the eggs during incubation for signs of life from the egg. Such signs of life may include an embryonic heartbeat, pulse, blood flow, staining with and detection of vitality dyes or the like. According to one embodiment, the implanted cells may be labeled to measure proliferation by dilution, in which the count per cell decreases although the overall count remains the same. For example, a cyanine dye, such as DiI may be used for fluorescently labeling membranes, or tritiated nucleotides may be used for radioactively labeling DNA. Other labels may permanently label cells, such as viral infection with a lentivirus expressing a fluorescent tag such as GFP, or an enzymatic tag such as luciferase. Such genetically encoded labels can be regulated by gene promoters or protein degradation tags such that their expression reflects intracellular metabolic events, such as cell cycle activity, mitochondrial membrane potential, protein synthesis etc. These labels can be measured by a vitality monitor 128 adapted to perform, among other techniques, fluorescence microscopy for DiI, GFP or the like, or MRI for tritiated probes or the like, and a luminescence counter for luciferase when the luciferin substrate is added to the exogenous material in the egg.

It will be appreciated that the vitality monitor may allow non-viable eggs to be identified early. Optionally, an egg removal system may be provided to remove such eggs from the biological collection system 200A (FIG. 2A).

It is noted that the period of incubation may be selected to be sufficient to allow engraftment of the population of cells to the chorioallantoic membrane (CAM) of the at least one fertilized egg.

The Applicator

The applicator 140 is configured to deliver exogenous material to the eggs. The applicator typically includes a delivery mechanism 142, a manipulator 144 and a feedback mechanism 146.

The delivery mechanism 142 is configured to deliver the exogenous material to the eggs. Exogenous material to be applied may be an implant such as a cell culture administered to the egg. For example, implants may include tumor cells, skin explants, biopsied material or the like. Such implants may be applied to fertilized eggs following an initial incubation period. Alternatively, or additionally, other exogenous material may include foreign bodies such as bacteria, viruses or external modulators.

As suits requirements, the delivery mechanism 142 may be adapted to inject the exogenous material into a compartment of the egg such as the amnion or yolk sac, or into a blood vessel of the egg, the embryo or the chorioallantoic membrane (CAM). Additionally or alternatively, the delivery mechanism 142 may be adapted to apply the exogenous material directly onto the chorioallantoic membrane (CAM).

It is noted that, as outlined below, in order to improve engraftment in the egg, the egg immune response may be reduced by irradiating, using X-rays, gamma rays or the like, prior to engraftment of the implanted cells. Accordingly, X-ray or gamma ray sources may be incorporated into the system, perhaps in compartments isolated by lead lining or the like. Alternatively, the system may be adapted such that where required, eggs may be removed and irradiated, perhaps automatically, as necessary. The system may be further configured to administer immunosuppressant drugs.

Accordingly, various applicators 140 may include delivery mechanisms 142 such as syringes, needles, cantilevered needle, jacketed needles, pipettes, multichannel pipettes, tweezers, magnetic droppers or the like.

Optionally, a reservoir 148 may be provided for storing the exogenous material before application to the egg. A reservoir may be provided including an agitator such as a stirrer or the like in order to maintain a constant composition of an agent to be delivered to the egg. Alternatively, or additionally, a reservoir may include an array of wells for containing agents of predetermined composition. For example, an 8×12 array of wells may contain material to be delivered by an eight channel pipette into an array of eggs. It will be appreciated that other configurations may occur to the practitioner. The material to be stored in the reservoir may be in liquid or in solid form. The reservoir may be used to form gel "plugs" (see "Identification and Delivering" section below) containing exogenous material or external modulators.

A label may be added to the exogenous material or external modulators, for example to assess whether the matter has entered the correct compartment of the egg upon delivery by the applicator. Thus for intravenous injection, a dye such as fast green may be added, or a blood vessel staining dye such as fluorescent dextrans, or a blood vessel restricted dye such as Evans Blue.

According to various embodiments, external modulators may include, but are not limited to, chemical agents, biological agents, radiation, mechanical aggression, thermal stress, contact sensitizers, allergens, gaseous agents, mechanical barriers and the like. Biological agents may include living cells or organisms, such as immune cells (including but not limited to T-cells, B-cells, NK cells and myeloid cells) or microbes.

Chemical agents may include surfactants, retinoids, carotenoids, food additives, moisturizers, mustard gas, organic molecules, inorganic compounds, vitamins, UV absorbing agents, UV protecting agents, perfumes, cosmetic formulations, lacquers, glues, paints, colorants, detergents, balms, creams, dyes, hair dyes, emulsions, gels, greases, shake lotions, pastes, oils, liposome formulations, lotions, mousses, ointments, suspensions, aqueous solutions, salves, solvents, shampoos, pollutants, steroids, shower gels, antibiotics, sulfa drugs, antiseptics, disinfectants, herbal formulations, anti-inflammatory agents, pharmaceutical compositions, aerosols, cleaning products, powders, petroleum jelly, anti-microbial agents, soaps, nail polish, acid rain, gasoline, kerosene, alcohols, industrial solvents, caustic chemicals, herbicides, metals, chelating agents, pesticides, mediations, fumigants, insecticides, fungicides, cleaning materials, contact sensitizers, allergens, impregnated dressings, solutions, occulative dressings, compression dressings, gallium compounds, kinase modulating agents, phosphate buffered saline (PBS), enzyme inhibitors, protease, secretions of plants and animals, endotoxins, antimicrobial formulations, tazarotene formulations, bexarotene formulations, azole formulations, topical antibiotic formulations (e.g. tetracycline family), plant derived toxins (e.g. poison ivy), animal-derived toxins, putative ameliorative agents (e.g. aloe vera), depilatory or hair growth-enhancing reagents, putative anti-aging formulations and the like as well as combinations thereof.

Biological agents may include, but are not limited to, hormones (e.g. estrogens), peptides, cytokines, chemokines, interferon formulations, nucleic acids, proteins, carbohydrates, carotenoids, lipids, fatty acids, prions, enzymes, lectins, antibodies and the like as well as combinations thereof.

In some embodiments the exogenous material may consist of an immobilising agent that is injected around the vicinity of the blood vessel that has been selected for injection by the applicator. The immobilising agent reduces the natural movement of the blood vessel, as well as providing contra to the impact of the injecting needle or catheter. The immobilising agent may comprise a cross-linking chemical that hardens albumen, for example.

Following application of exogenous material, the eggs together with the exogenous material may be returned to the incubator for an additional period for continued incubation. During this second period, anastomosis of the host and implant blood vessels may occur, where there are extant blood vessels in the engrafted implant material. For exogenous material lacking extant blood vessels, the chick vasculature generates a de novo blood vessel network in the impalnted material. The implant is typically nourished by the chick's blood and gases exchanged by chick erythrocytes. It may therefore be necessary to isolate the implant from microbes in the ambient atmosphere outside of the egg shell which could contaminate the incubating implant and possibly lead to tissue degradation. Possible means for isolating the implant or sealing the egg include, but are not limited to, placing of an egg sealing unit (see FIG. 10), covering with saran wrap, adhesive tape, the egg shell itself, glass-coverslips sealed with wax, providing a sterile environment and the like.

In some embodiments, the environment provided during the second incubation period may differ from that during the initial incubation period, for example, by selecting chemical compositions or exposure to radiation which may influence the development of the implants such that environmental conditions may be tested.

The manipulator 144 is provided to manipulate the delivery mechanism 142 relative to the egg. This is necessary in order for the delivery mechanism 142 to bring the exogenous material to the desired region of the egg without damaging the egg. For example, where the delivery mechanism 142 is required to inject material into a blood vessel, the manipulator 144 is operable to direct the injection head of the delivery mechanism to the relevant blood vessel and at the required angle of attack. Similarly, where a cell culture is to be applied to the chorioallantoic membrane (CAM), for example, the manipulator 144 is operable to bring the delivery mechanism 142 into the desired region without damaging the surrounding tissue.

Various manipulators may be utilized in embodiments of the automated biological sampling system 200A (FIG. 2A). These include micromanipulators, robotic arms, articulated arms, telescopic arms, tracks, runners and the like as well as combinations thereof.

According to various embodiments, the manipulator 144 may be operable to act upon the delivery mechanism 142, moving it into position relative to the egg. Alternatively, the manipulator 144 may be operable to move the egg into position relative to the delivery mechanism 142, possibly by manipulating the egg support apparatus 180.

In order to control the movement of the manipulator 144, the feedback mechanism 146 is operable to provide feedback. The feedback mechanism 146 typically includes at least one sensor configured to sense the position of the delivery mechanism 142 relative to the egg, and a processor operable to direct the manipulator 144 to the desired position. Various feedback sensors may be used for such an arrangement; these include video sensors, sonar, shadow contrast detectors, interferometers, piezoelectric elements, tuning forks and combinations thereof.

For example, a CCD camera may be linked to a feedback system to control a robotic arm manipulating the delivery system. Fine control in the approach to the target region may be supplemented by interferometric analysis of a laser beam reflected from the surface of the target region, alternatively or additionally, a piezoelectric element attached to at least one tine of a tuning fork may be used to monitor changes in the resonant frequency of the tuning fork as it approaches the surface. Other feedback mechanisms may be preferred as suit requirements.

The Shell Removal Mechanism:

In some embodiments, the system 200A (FIG. 2A) may further include a shell removal mechanism. The shell removal mechanism is provided to remove at least a section of the shell in order to provide access to the chorioallantoic membrane (CAM) and the embryo within.

Where only a section of the shell is to be removed, the shell removal mechanism may include a cutter for slicing a ring around the egg, and a sucker for removing the cut ring. Where a shell-less egg is required the shell removal mechanism may be configured to break the fertilized egg into a suitable egg support apparatus 180.

Optionally, the shell removal mechanism comprises an electric drill to expose the chorioallantoic membrane (CAM) delineated vascular system.

It is noted that only eggs on which a distinct fine vascular system can be recognized on the chorioallantoic membrane (CAM) is suitable for testing. This is sometimes considered a critical criterion to develop a successful assay, and may lead to a selection procedure, where required.

To improve imaging or visualization of the CAM blood vessels, a small area of CAM itself may be removed, since it is opaque and interferes with light transmission, reducing accuracy of injections and imaging and the like. To prevent leakage of egg material upon CAM section removal, a sealing gel may be applied to the hole in the CAM, whose properties are compatible with needle penetration and resealing after removal, as well as being mostly translucent for accurate imaging and needle guidance.

The Egg Support Apparatus:

The egg support apparatus 180 may be provided in order to hold the eggs in the sample collection system 200A (FIG. 2A). Accordingly, the egg support apparatus 180 is typically a tray having an array of stands for supporting the eggs within the system 200A (FIG. 2A). As noted above, where shell-less eggs are to be incubated, the egg support apparatus 180 may have suitably adapted receptacles, for example cups with covers. Optionally, such receptacles may be disposable.

According to some embodiments, the egg support apparatus may be constructed from transparent material, such as glass, PVC or the like. It will be appreciated that such a construction would allow imaging of the eggs contained by the egg support apparatus from various angles.

Apart from containing the eggs within the system 200A (FIG. 2A), the egg support apparatus 180 may have additional functionality as required. For example, the egg support apparatus may be adapted to provide a turning motion to the eggs during incubation.

Typically, the egg support apparatus 180 is adapted to move between various zones of the system 200A (FIG. 2A). For example, a tray supporting an array of eggs, may be mounted upon a rail and adapted to move between separate compartments or chambers for incubation, application of exogenous material and/or sampling.

Furthermore, the egg support apparatus 180 may itself form part of the manipulator 144 for positioning the egg relative to the delivery mechanism 142.

Figure 6:
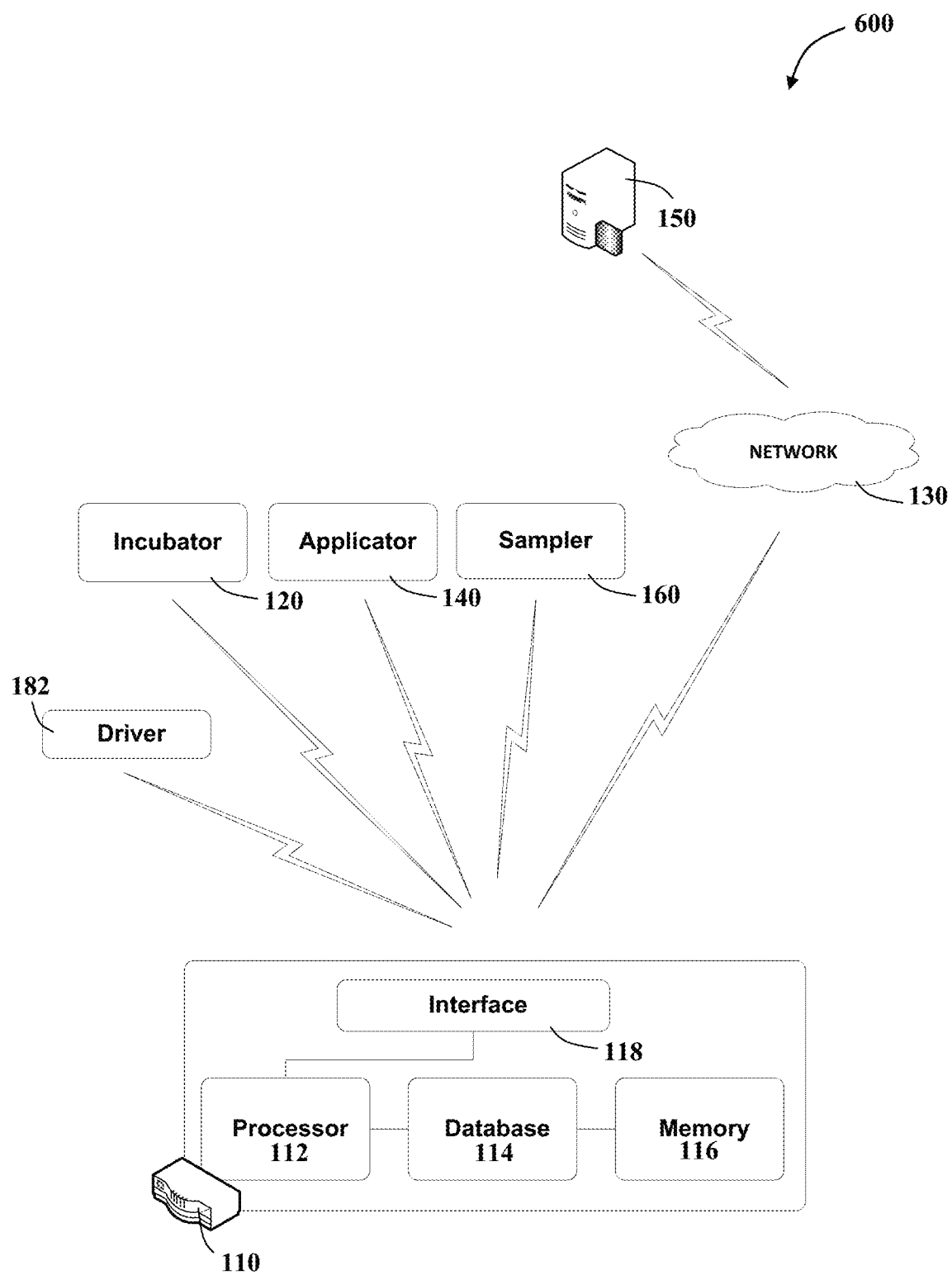
FIG. 6 is a block diagram of a distributed biological sampling system for performing assays automatically on embryonated eggs.

Optionally, the egg support apparatus 180 is controllable via a driver 182 (FIG. 2B, FIG. 6) operable to receive commands via the user interface (FIG. 6, item 118) of the system controller (FIG. 2A, FIG. 2B, FIG. 6 item 118).

The Sampler:

The sampler 160 is provided to collect biological samples from the eggs. Sampling may be invasive, possibly even destructive to the egg. Additionally or alternatively, non-invasive or remote sampling may be preferred.

For example, material may be removed invasively for analysis, biopsy, assay and the like. Removed material may be used in biological analysis techniques such as, but not limited to, Polymerase Chain Reaction (PCR), Fluorescence-Activated Cell Sorting (FACS), Flow Cytometry (FCM), Enzyme-Linked Immunosorbent Assay (ELISA), Enzyme-Linked Immunosorbent Spot (ELISPOT), Enzyme Multiplied Immunoassay Technique, RAST test, Radioimmunoassay, Immunohistochemistry, Immunofluorescence, dye absorption, enzymatic activity and the like. Chemical analyses of the sampled material may include spectrophotometry, HPLC, mass spectrometry, for determining the concentration of external modulators in the sampled material. Indeed, where required, the system 200A (FIG. 2A) may incorporate any or all of these material analysis devices.

Alternatively, samples may be obtained non-invasively using imaging techniques such as photographic imaging, radiographic detection, Magnetic Resonance Imaging (MRI), fluorescence imaging, luminescence imaging, ultrasonic imaging, heat detection, x-ray imaging, scintigraphy, Positron Emission Tomography (PET), photoacoustic imaging, thermography, and the like as well as combinations thereof. Indeed, where required, the system 200A (FIG. 2A) may incorporate any or all of these non-invasive sampling devices.

It will be appreciated that non-invasive sampling may be useful, particularly where ongoing monitoring is required. For example, the sampler 160 may be configured to periodically take measurements from the egg during incubation.

Still another method of sampling may be to install a catheter or similar device into a blood vessel or one of the liquid compartments with a valve that can be opened, in order to take multiple samples. For example, a needle attached to fine silicon tubing may be inserted into a chorioallantoic membrane (CAM) vessel, with a valve that can be opened for sampling blood at desired intervals.

Figure 3A:
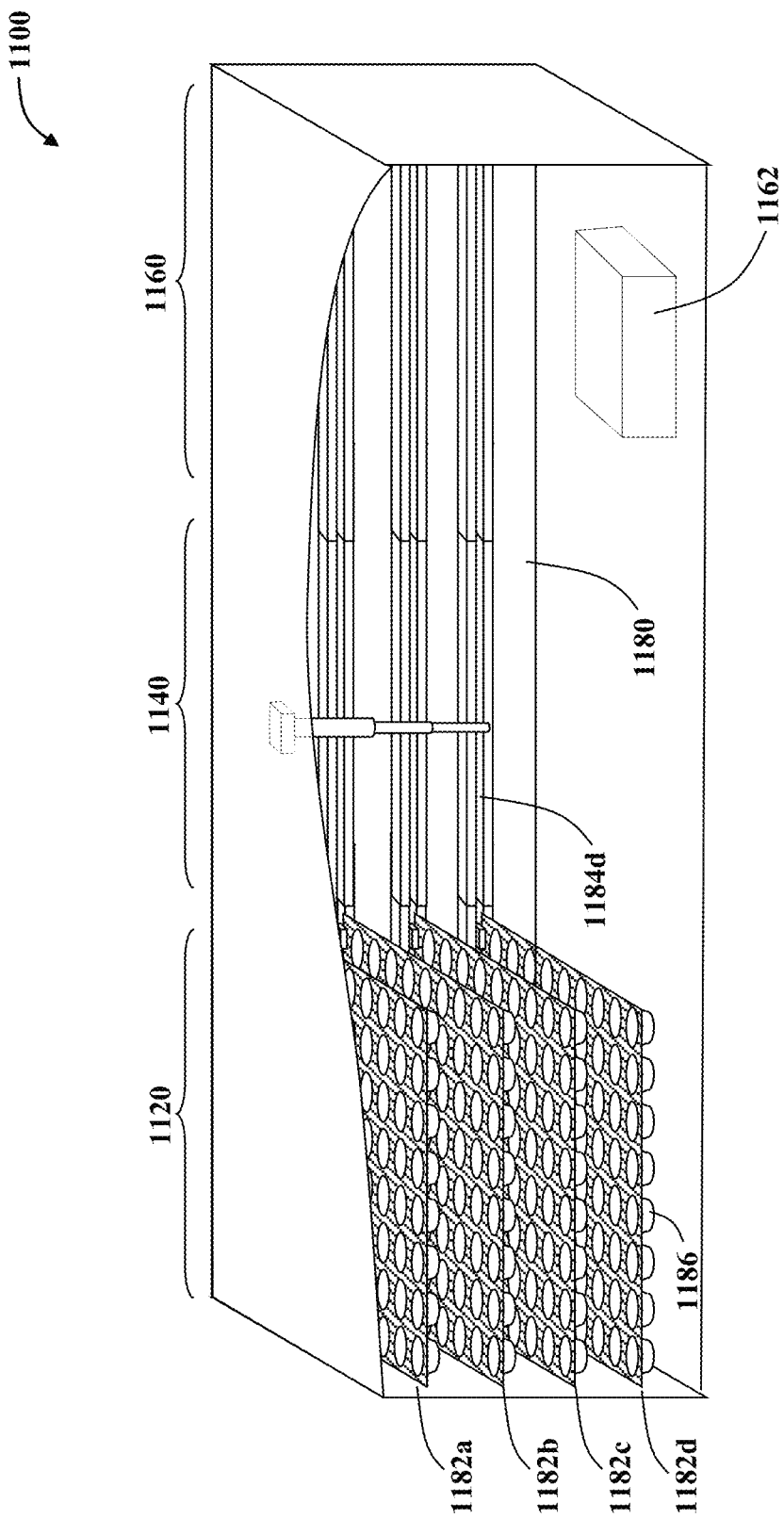
FIGS. 3A and 3B are schematic cut away isometric projections representing an embodiment of a biological sample collection system.
Figure 3B:
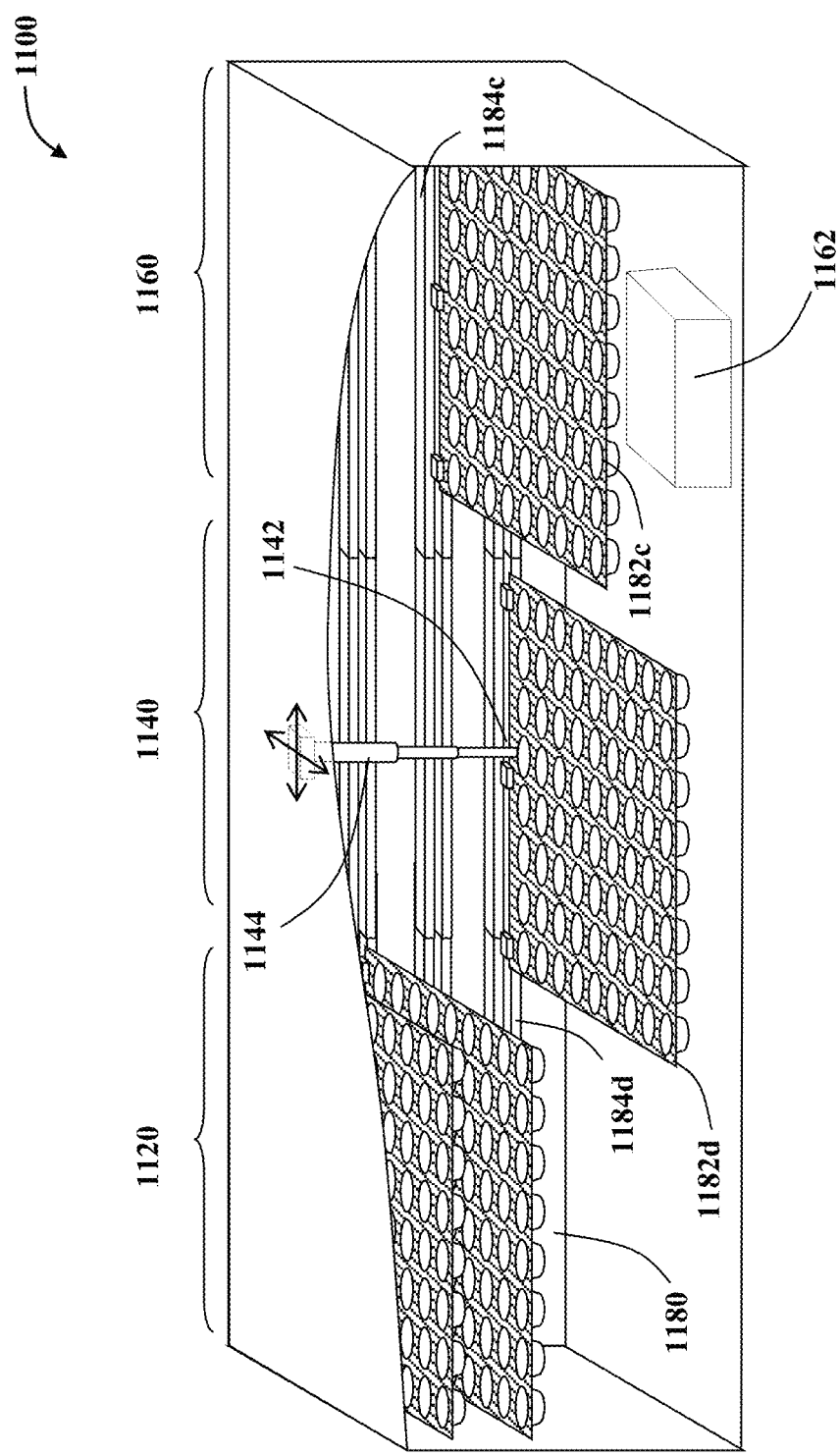

Detailed Projections:

In order to further illustrate the various embodiments of the system, reference is now made to FIGS. 3A and 3B which show schematic cut away isometric projections representing one embodiment of a biological sample collection system 1100.

The embodiment includes an incubation chamber 1120, an application chamber 1140 and a sampling chamber 1160. The egg support mechanism 1180 includes multiple trays 1182a-d mounted upon tracks 1184a-d.

The egg support trays 1182a-d are provided to contain fertilized eggs. In the example provided in FIGS. 3A and 3B, each tray includes a 9×8 array of egg receptacles 1186. Where appropriate, the receptacles may be configured to contain complete eggs, shell-less eggs or partially shell-less eggs. It will be appreciated that the 9×8 array of the example may be of particular use where an eight channel syringe is used to apply exogenous material to the eggs, for example, when such matter is applied manually. Other configurations may be preferred as suit requirements.

The trays 1182a-d are mounted on tracks 1184a-d which extend through all three chambers 1120, 1140, 1160 and along which the trays may be moved. With particular reference now to FIG. 3A, showing the automated system 1100 during one of the incubation phases, all the trays 1182a-d are arranged in the incubation chamber 1120.

The incubator is configured to keep the incubated eggs at a temperature of approximately between 30 to 40 degrees Celsius so as to maintain an environment suitable for the continued viability of fertilized eggs. It will be appreciated that a turning mechanism (not shown) may be provided to periodically tilt the trays to simulate the turning of eggs during natural incubation.

Reference is now made to FIG. 3B, there is provided the automated system, which is generally indicated at 1100, showing an alternative configuration; the one tray 1182d has been transferred, along its associated track 1184d, to the application chamber 1140, for introduction of exogenous material to the eggs and another tray 1182c has been transferred to the sampling chamber 1160.

In the application chamber 1140, a delivery mechanism 1142 mounted to a manipulator 1144 may be directed to a selected egg within the tray 1182d. The manipulator 1144 of the example includes a roof mounted telescopic arm configured to move the delivery mechanism 1142 to the desired position within the application chamber. It will be appreciated that other manipulators may be additionally or alternatively provided as required.

The tray 1182c is shown transferred to the sampling chamber 1160 wherein it may be inspected using an imager 1162. Various imagers 1162 may be utilized in the automated system 1100 as outlined herein. Additionally or alternatively, material may be collected from the eggs for analysis.

In order to prevent movement of the embryo during application of the exogenous material, the application chamber 1140 may be cooled to a low temperature such as around 18 degrees Celsius or so. Accordingly, an insulating partition (not shown) may be provided between the incubation chamber 1120 and the application chamber 1140.

The application chamber 1140 may be adapted for other methods for preventing movement such as applying gentle suction to the membrane or dropping sterile filter paper rings onto the chorioallantoic membrane (CAM) to maintain stretched blood vessels for injection/removal of blood.

Following application of the exogenous material, the tray 1182d may be returned to the incubation chamber for additional periods of incubation. The process may be repeated a plurality of times with different exogenous materials being applied. For example, an incubated egg may be transferred to the application chamber 1140 initially for application of an implant or the like. Then, the egg may be returned to the incubation chamber 1120 for further incubation until the engraftment of the implant occurs. The egg may be returned to the application chamber 1140, following re-incubation so that an external modulator, such as described above, may be applied to the egg. The egg may be transferred again to the incubation chamber 1120 for further incubation during which the egg may be periodically transferred to the sampling chamber 1160 for examination.

It will be appreciated that the three chambered system 1100 described hereinabove in relation to the embodiment of FIGS. 3A and 3B represents only an example of a possible biological sampling system. Alternatively, other embodiments may be preferred to suit different requirements.

Figure 4A:
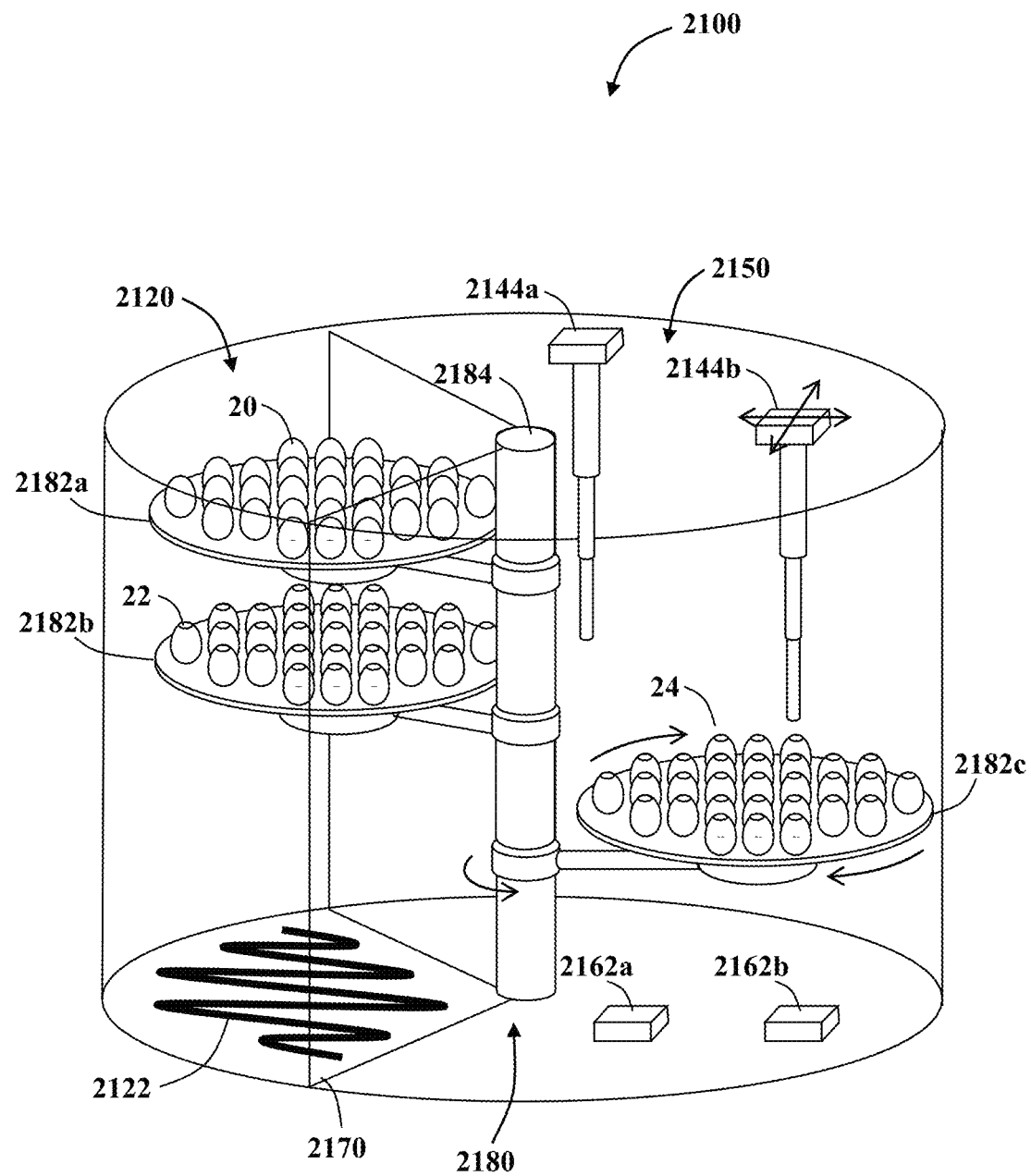
FIG. 4A is a schematic isometric projection representing a further embodiment of a biological sample collection system.

Reference is now made to FIG. 4A, there is provided a schematic isometric projection representing a further embodiment of an automated biological sample collection system, which is generally indicated at 2100. The automated system 2100 of the embodiment of FIG. 4A includes an incubator compartment 2120, a second compartment 2150 and an egg support apparatus 2180.

The incubator compartment 2120 has a convection heater 2122 and an air circulator or filtration system or the like. The second compartment 2150 is a multifunctional space which may include various mechanisms such as manipulators 2144a, 2144b, samplers 2162a 2162b, shell removal mechanisms (not shown) and the like. Partitions 2170 may be provided to divide the separate compartments; such partitions may be insulated and/or sealed to allow the separate compartments 2120, 2150 to support different environmental conditions.

The egg support apparatus 2180 of the embodiment of FIG. 4A includes multiple egg trays 2182a-c coupled to a central support column 2184 in a manner that allows rotation. The trays 2182a-c are configured to individually rotate around the central support column 2184 such that each tray may be transferred from the incubator compartment 2120 to the second compartment 2150. Optionally, the trays 2182a-c may be further configured to rotate about their central axes to position the eggs 20 supported thereby.

In the example, a first tray 2182a is shown supporting complete eggs 20 during an incubation phase. Following an initial incubation period, the tray may be transferred to the second chamber 2150 where a shell removal mechanism, such as described herein below in relation to FIG. 4B, may be used to remove a section of the egg shell, and the applicator may be used to apply exogenous material to the egg. A second tray 2182b is shown supporting eggs 22 which have had the top section of their shells removed, typically, such eggs may be returned to the incubator for a second incubation period following the application of exogenous material.

The third tray 2182c is shown supporting eggs 24 following a second incubation period after which the eggs 24 have been transferred into the second chamber 2150 for application of additional exogenous material, for example, an external modulator such as described hereinabove or the like.

Figure 4B:
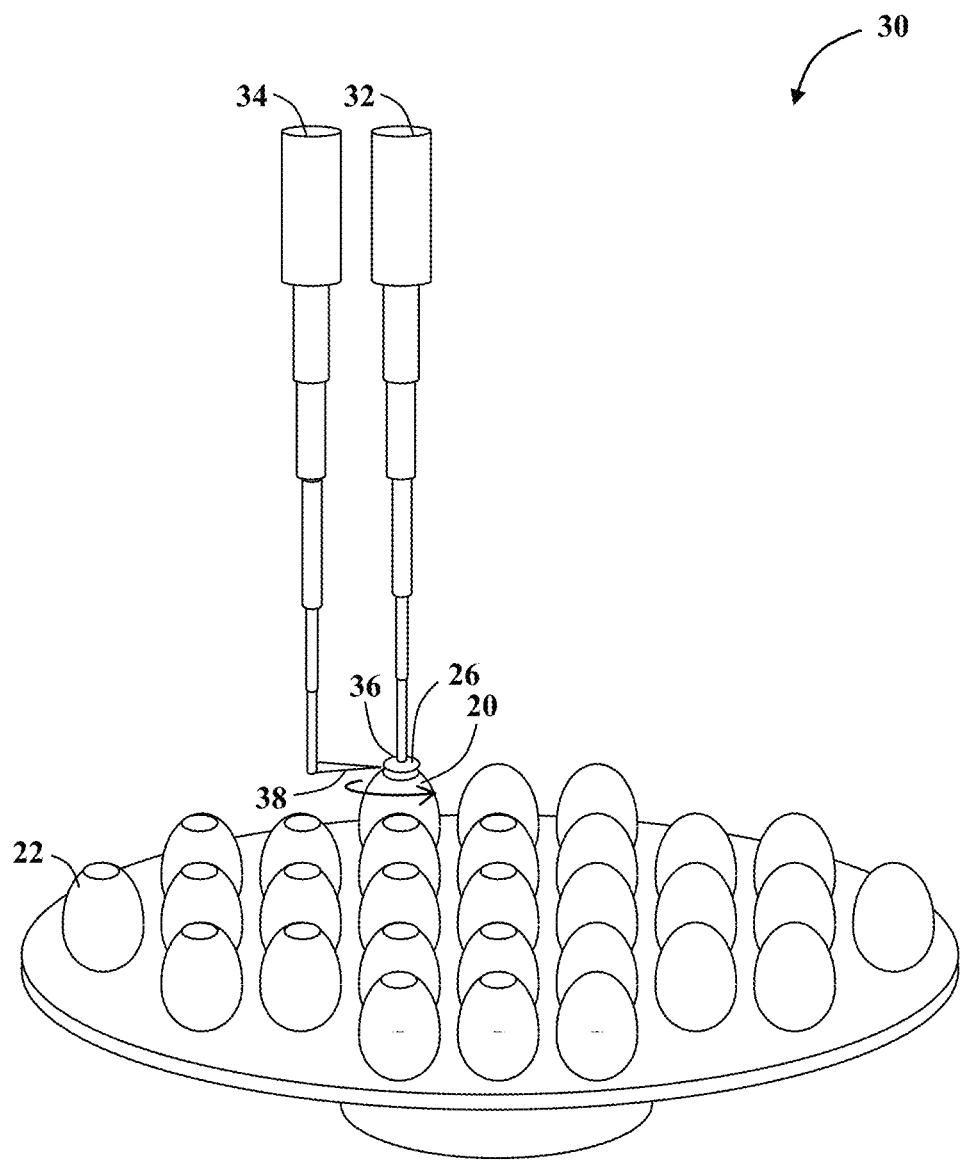
FIG. 4B shows a possible shell removal mechanism for use in embodiments of the biological sample collection system.

Reference is now made to FIG. 4B, there is provided a possible shell removal mechanism, which is generally indicated at 30, for use with embodiments of the automated biological sample collection system. The shell removal mechanism 30 includes two manipulators 32, 34. The first manipulator 32 has a suction head 36 operable to engage the top section 26 of the egg shell of an egg 20. The second manipulator has a blade head 38 configured to sever the top section 26 from the egg 20. Optionally, each egg may be rotatable individually to further manipulate the egg's position. Other shell removal mechanisms 30 are known and may occur to the skilled practitioner.

Figure 5A:
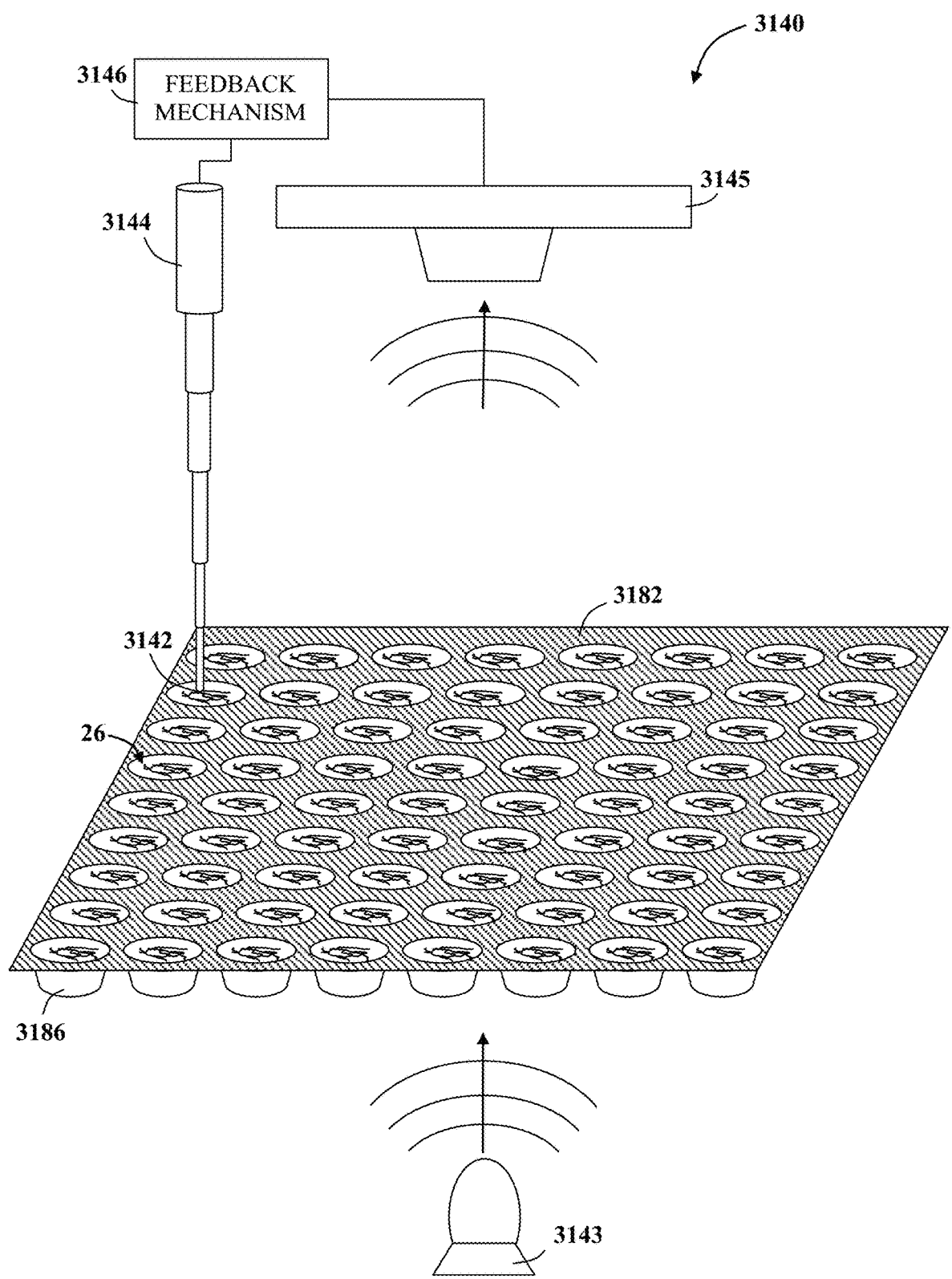
FIG. 5A schematically represents a possible applicator for use with the biological sample collection system.

Reference is now made to FIG. 5A, there is provided a schematic representation of a possible applicator, which is generally indicated at 3140, for use with an automated biological sample collection system and a tray 3182 of receptacles for containing shell-less eggs. The applicator 3140 includes a delivery mechanism 3142, a manipulator 3144, an illuminator 3143, a detector 3145 and a feedback mechanism 3146.

The tray 3182 contains egg receptacles 3186. The egg receptacles 3186 are preferably made of a material transparent to the type of radiation emitted by the illuminator 3143 such that the detector 3145 is able to monitor the relative positions of the delivery mechanism 3142, the organs of the shell-less eggs and their embryos contained within the receptacles 3186.

The detector 3145 is typically in communication with the feedback mechanism 3146 which is operable to direct the delivery head 3142 accordingly.

Figure 5B:
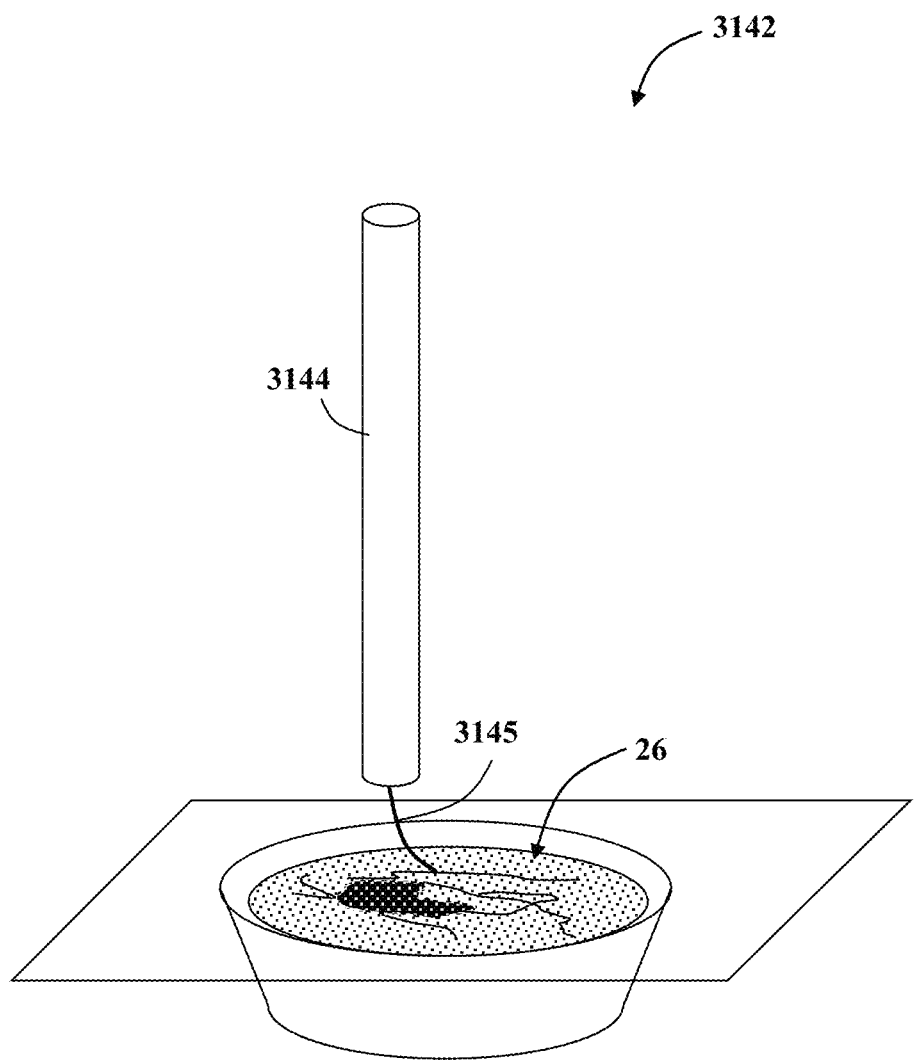
FIG. 5B schematically represents a possible embodiment of the delivery mechanism being used to inject exogenous material into the chorioallantoic membrane (CAM) of a shell-less egg.

Reference is now made to FIG. 5B, there is provided a possible embodiment of the delivery mechanism, which is generally indicated at 3142, for delivering exogenous material. The delivery mechanism 3142 includes an angled needle 3145 which may be used to inject the exogenous material into the chorioallantoic membrane (CAM) of a shell-less egg 26 or other organs or blood vessels.

The Controller:

Referring back to the block diagram of FIG. 2A, in order to control and coordinate the automated biological sample collection system 200A, a controller 110 may be provided. The controller 110, which may be in communication with the various functional elements, may be operable to perform a sequence of steps according to an algorithm and support the required automation.

Accordingly, the controller 110 may be functional to coordinate steps such as incubation conditions, incubation periods, calculation of incubation periods, selection of incubation periods, transfer of eggs from the incubator to the applicator and/or sampler, applicator control, detection of non-viable eggs, removal of non-viable eggs, image analysis, coordination of feedback for the manipulator, shell removal, sampler activation, data collection and the like.

Where appropriate the controller 110 may include a processor, a database, a memory and/or a user interface as required. The controller 110 may further be operable to support remote communications as illustrated in FIG. 6, hereinafter.

Reference is now made to FIG. 6, there is provided a block diagram of a distributed biological sampling system, which is generally indicated at 600, for performing assays automatically on embryonated eggs. The distributed biological sampling system 600 includes a system controller 110 operable to automatically control and monitor the system, where the system controller 110 is in communication with the incubator 120, the applicator 140 and the sampler 160. The system controller 110 comprises a processor 112, a database 114, and a memory 116 and operable to communicate with the various external elements via a user interface 118.

The system controller 110 is further operable to communicate with the driver 182 which is configured to drive the egg support apparatus 180 according to assay specifications.

Furthermore, the system controller 110 may be operable to communicate remotely with a server 150 via a communication network 130 such as the Internet. This may support controlling and monitoring the automated sampling system centrally and further perform the required analysis of the sample or associated imaging.

Where appropriate, the controller software is operable to configure system settings such as, harvesting date and time; an engrafting date and time; an injecting date and time, and the like.

The controller software is further operable to identify the peak time for harvesting and the experimental mode may be used to determine days upon which the sample cell may be extracted.

As appropriate, the system controller is operable to check if the drug applied is absorbed, which may be executed in various ways, such as monitoring the absorption of the bolus by monitoring blood leakage from a blood vessel or detecting a bolus ejected from the egg, for example using dyes and the like that have been added to the exogenous material or external modulators, prior to injection or delivery. Additionally or alternatively, the delivered drug may be labeled such that its arrival at the target cells may be confirmed. Other secondary effects may be monitored as will occur to those in the art. For example, cell membrane movement is affected by chemotherapy agents within minutes of drug application, and can be monitored using fluorescence imaging of fluorescently labeled cell membranes.

In such cases where a failed drug delivery is observed, it may be desirable to reject the egg or to retry the injection as appropriate.

Blood Vessel Detection:

The chick embryo has been extensively used to answer very different questions at different stages of development. The avian embryo develops a structure for gas exchange with its environment that has some of the same functions as the mammalian placenta. The chorioallantoic membrane (CAM), with its capillary bed, is the respiratory organ of the chick embryo until the 19th day of incubation, at which time the embryo pips internally in the air cell and starts air breathing, thus it has become an attractive model for study and research.

The circulation in the chick embryo is comparable to that of the mammalian fetus. The left and right chorioallantoic arteries bring the deoxygenated blood into contact with the chorioallantoic membrane (CAM) where gas exchange through the egg shell occurs and the chorioallantoic vein returns the oxygenated blood to the embryo. These vessels are equivalent to the umbilical circulation. After opening the air cell and the extra embryonic membranes, by a shell removal mechanism, these vessels are easily accessed. Further, using various automated technologies using transducers and imaging the veins appropriate for injection may be exposed.

Optionally, the shell removal mechanism comprises an electric drill to expose the chorioallantoic membrane (CAM) delineated vascular system.

It is noted that only eggs on which a distinct fine vascular system can be recognized on the chorioallantoic membrane (CAM) is suitable for testing. This is considered a critical criterion to develop a successful assay.

It is further noted that the sampler when placed where the chorioallantoic membrane (CAM) is to be assessed should be illuminated in such a way to avoid shadows and high temperatures for the eggs.

The blood vessels of the embryo may be identified, in particular the main vessel, the umbilical vein which is connecting the chorioallantoic membrane (CAM) and the embryo. It is known that blood flows from chorioallantoic membrane (CAM) to the embryo through the umbilical vein. This may facilitate detection of the direction of blood flow. If the umbilical vein is not always connected to the air pocket (FIG. 1A, item 70) then it may be useful to move the air pocket to the position of the umbilical vein.

Additionally, shining a light through the shell may allow to see the positions of other blood vessels. Identification of other blood vessels carrying blood towards the chorioallantoic membrane (CAM) may be useful as it allows exogenous material to be injected in the direction of the chorioallantoic membrane (CAM) directly without the material first passing through the embryo. This is particularly important when injecting "T-Cells" into veins as such T-cells may be large and prone to getting stuck in the capillaries of the embryo, thus it is important to determine whether blood flow is to the chick body or to the CAM, as well as determining the loss of exogenous T-cells in the blood due to their inability to pass through chick capillaries or organs (e.g., liver), in each direction.

Injection into arteries generally causes bleeding that can lead to loss of chick viability and leakage of the external modulators or exogenous material being injected. Injecting into veins causes much less damage to the chick or loss of injected material. By injecting in the direction of the blood flow there is less resistance to the injection pressure applied by the applicator, and thus less chance of damage to the injected blood vessel. Slow, continuous injection of material further improves blood vessel recovery following injection. In one embodiment, an intravenously inserted catheter connected to a pump to inject material in the direction of venous blood flow, may provide the appropriate conditions for achieving minimal loss in chick viability and maximal delivery of injected material.

The diagrams of FIG. 1B, hereinabove and FIG. 8 hereinafter, illustrating a blood vessel network and other organs of importance for performing engraftment and injections of the exogenous material into the chorioallantoic membrane (CAM) or into other organs of an embryonated egg.

Analysis:

The software of the system controller is operable to perform the various aspects of a desired assay, using automatically controlled components such as an imaging unit (FIG. 2B), feedback sensors, mechanical elements and the like.

Various feedback sensors may be used for such an arrangement; these include video sensors, sonar, shadow contrast detectors, interferometers, piezoelectric elements, tuning forks and combinations thereof.

For example, a CCD camera may be linked to a feedback system to control a robotic arm manipulating the delivery system. Fine control in the approach to the target region may be supplemented by interferometric analysis of a laser beam reflected from the surface of the target region, alternatively or additionally, a piezoelectric element attached to at least one tine of a tuning fork may be used to monitor changes in the resonant frequency of the tuning fork as it approaches the surface. Other feedback mechanisms may be preferred as suit requirements.

Figure 7:
FIG. 7 is a block diagram demonstrating possible actions along a time axis of incubation days.

Reference is now made to FIG. 7, there is provided the block diagram, which is generally indicated at 700, demonstrating possible actions along a time axis of incubation days.

The block diagram 700 illustrates an initial incubation period A of a duration according to the requirements of a specific assay. The initial incubation period may be followed by a pricking step 702, which may be followed immediately by a delivering step 704. Alternatively, the delivering step may be delayed for a time duration, according to the assay specification and requirements. Following the delivering (of exogenous materials), an additional incubation period may take place D for a duration according to the specification or requirements of the assay. The additional incubation period may be followed with collecting of samples 706. Additionally or alternatively, the step of delivering may be repeated, according to assay specification, in which each delivery may be followed with an additional incubation period.

The final step is performing analysis 708 to the samples collected. Additionally or alternatively, the embryo may be analyzed, including imaging throughout the process or at specific time periods.

Identification & Delivering:

The classical assays for studying angiogenesis in vivo include the chick embryo chorioallantoic membrane (CAM). The chorioallantoic membrane (CAM) was first used to study tumor angiogenesis by grafting tumor samples onto its surface on day 8 of incubation. Since then, the chorioallantoic membrane (CAM) assay has been used to identify almost all of the known angiogenic factors and to assess the angio static activity of a variety of natural and synthetic compounds.

Figure 8:
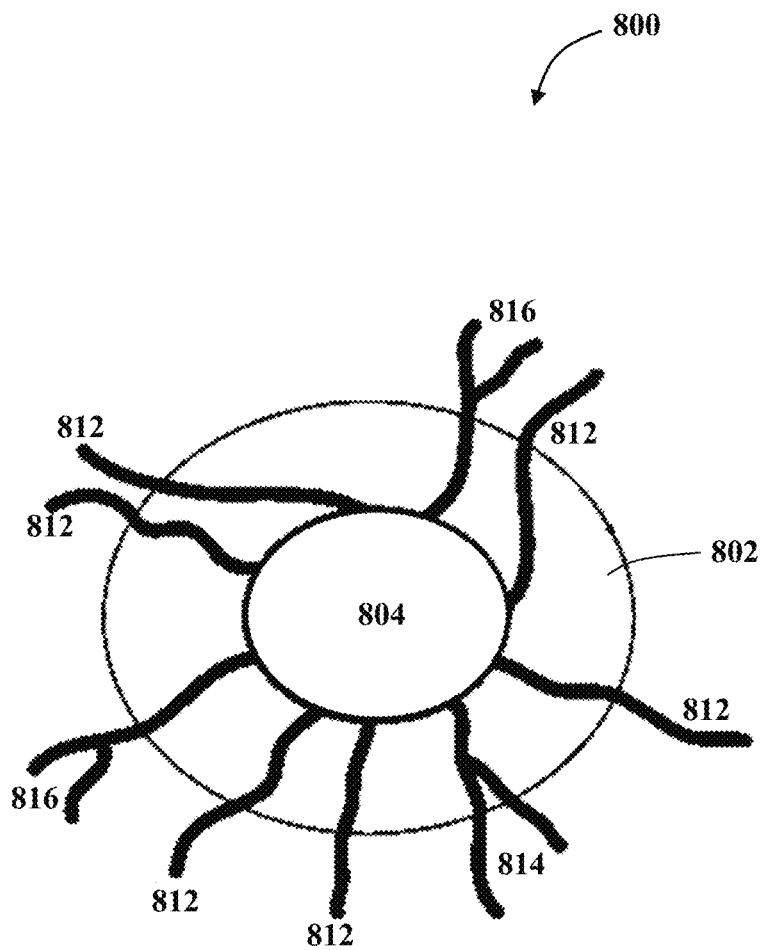
FIG. 8 is an illustrative example of different blood vessels branching onto a chorioallantoic membrane (CAM), observed after implanting.

Reference is now made to FIG. 8, there is provided an illustrative example of different blood vessels branching, which is generally indicated at 800, demonstrating responses around an implant, for example, onto a chorioallantoic membrane (CAM), observed after implanting.

The illustrative example 800 includes partial sectional top view of the chorioallantoic membrane (CAM) 802, the transplant 804 and various blood vessel such as: blood vessels with no branching 812; blood vessels with branching around the transplant 814; and blood vessels with branching further out of the transplant.

Figure 9A:
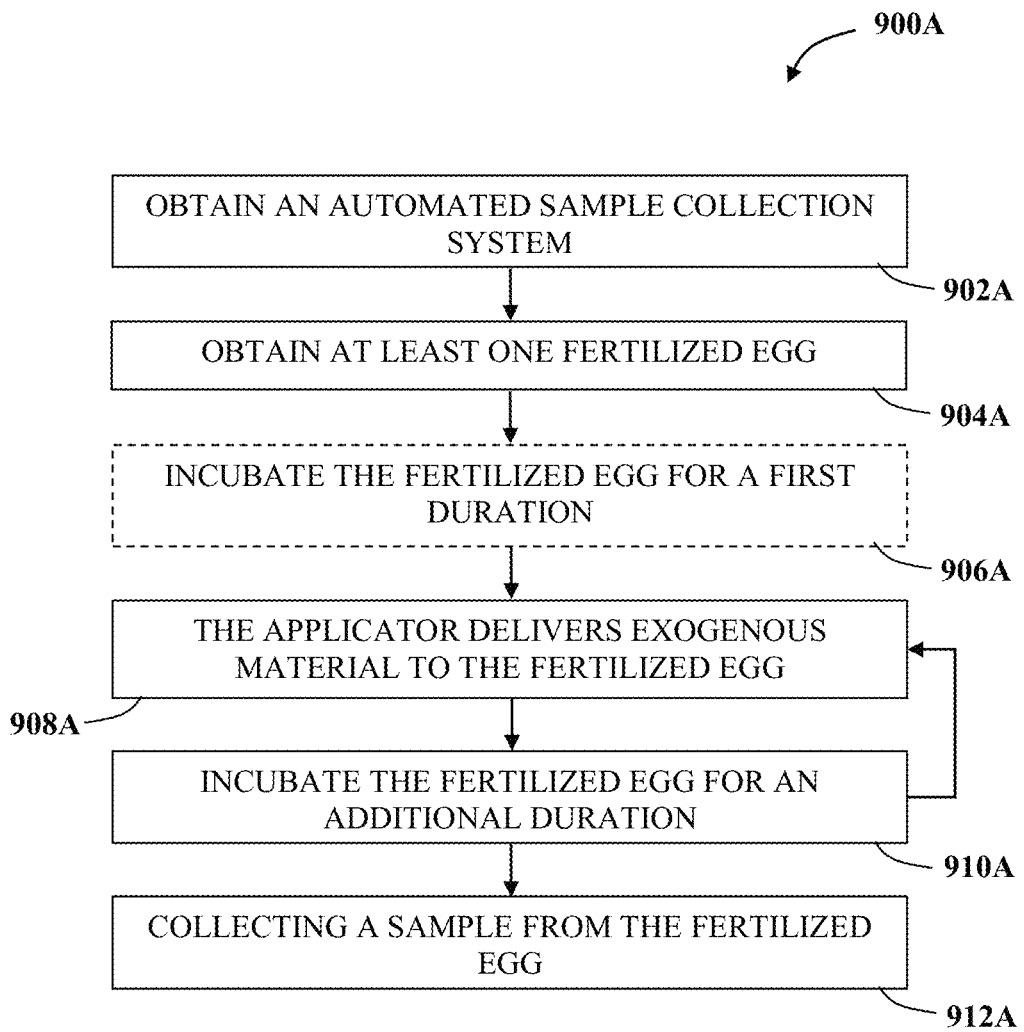
FIG. 9A is a flowchart representing a method for use with the automatic collection of biological samples from avian eggs.

Reference is now made to the flowchart of FIG. 9A, there is provided a possible method, which is generally indicated at 900A, for use with the automated system for the collection of biological samples. The method includes the steps:

In step 902A, obtaining an automated sample collection system such as described hereinabove;

In step 904A, obtaining at least one fertilized egg;

In step 906A, optionally, incubating the fertilized egg for a first duration period;

In step 908A, an applicator delivering exogenous material to the fertilized egg;

In step 910A, incubating the fertilized egg for an additional duration period; and In step 912A, collecting at least one sample from the fertilized egg.

Where appropriate, step 908A may be further subdivided into the steps:

removing at least a part of the egg shell of the fertilized egg thereby exposing at least part of the chorioallantoic membrane (CAM); and placing a population of cells in contact with the chorioallantoic membrane (CAM).

It is noted that step 908A and step 910A may be repeated a plurality of times, for example, where a variety of types of exogenous material are to be applied. Thus, where required, a population of cells may be applied to the chorioallantoic membrane (CAM) of a fertilized egg and the fertilized egg then returned to the incubator for a period of time sufficient to allow engraftment of the implant to occur. The applicator may then be used to deliver another exogenous material such as a chemical or biological agent before again incubating the fertilized egg.

Where appropriate, the method may further include the steps of removing a part of the egg shell of the fertilized egg, or removing the whole egg fertilized shell, thereby exposing and providing access to the chorioallantoic membrane (CAM). The modulator may be administered using a variety of techniques, such as topical administration, subcutaneous administration, injection into the explant, injection into the explant vasculature, injection into fertilized egg vasculature and the like, as well as combinations thereof.

It is further noted that, in order to improve engraftment in the fertilized egg, the fertilized egg immune response may be reduced by irradiating, using X-rays, gamma rays or the like, prior to engraftment of the implanted cells. Such irradiation may inhibit the normal xenograft rejection of an intact host immune system. Furthermore, for engraftment of blood and bone marrow malignancies, irradiation may make hematopoietic niches available to absorb the donor cells in the host bone marrow. It is noted that such irradiation typically leaves the egg host free of compounds that may interfere with the growth of the graft in the therapeutic conditions that are being tested. Additionally or alternatively, other immunosuppressant drugs such as cyclosporine or the like may be used to improve engraftment due to immunosuppression of the host rejection response, as well as the anti-apoptotic effect that may limit graft cell death.

Figure 9B:
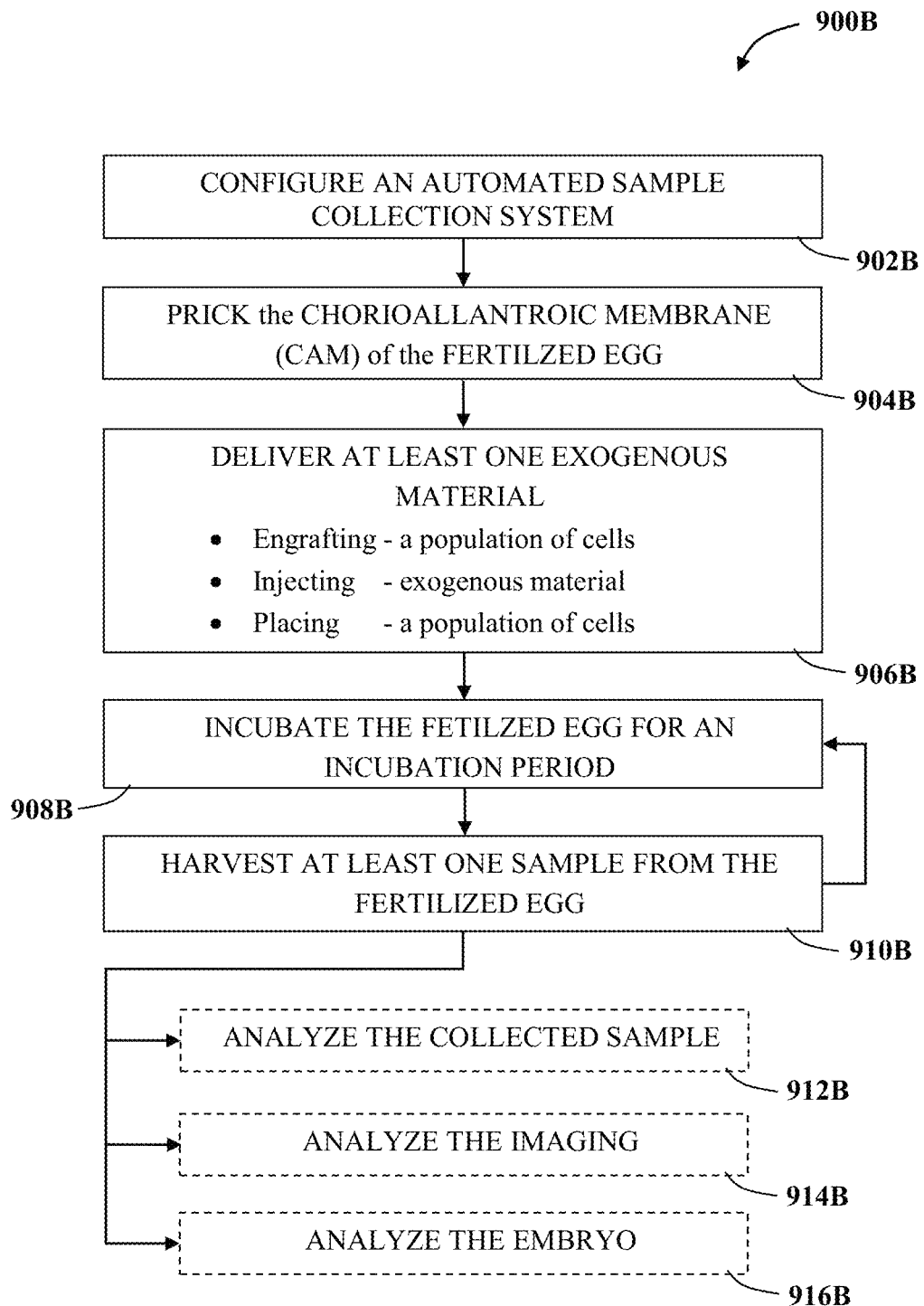
FIG. 9B is a flowchart representing another method for use with the automatic analysis of collected biological samples from avian eggs.

Reference is now made to the flowchart of FIG. 9B, there is provided another possible method, which is generally indicated at 900B, for use with the automated system for the collection of biological samples. The method includes the steps:

In step 902B, configuring an automated sample collection system according to the desired assay;

In step 904B, pricking the chorioallantoic membrane (CAM) of the at least one fertilized egg. Optionally, this step may be carried out by a shell removal apparatus such as described in FIG. 4B;

In step 906B, delivering at least one exogenous material to the fertilized egg, by an applicator. Where appropriate, the step further comprises various activities according to the assay specification such as: engrafting, by the delivery mechanism (FIG. 2A, item 142), a population of cells to the chorioallantoic membrane (CAM); placing, by the delivery mechanism (FIG. 2A, item 142), a population of cells in contact with the chorioallantoic membrane (CAM); and injecting, by the delivery mechanism (FIG. 2A, item 142), exogenous material into a designated blood vessel of chorioallantoic membrane (CAM) or into other elements of the embryonated egg. A population of cells may also be applied as a solid mass contained within a pre-formed gel "plug" (such as matrigel, collagen, alginate or the like). A gel plug containing high levels of pro-angiogenic agents may greatly improve the rate of engraftment success, especially when smaller numbers of cells are incorporated in the plug.

In step 908B, incubating the fertilized egg for an additional duration period; and In step 910B, harvesting at least one sample from the fertilized egg, by the sample collector.

Where appropriate, step 902B may be further subdivided into the steps:

setting various configuration parameters associated with the automated sampling system such as: a harvesting date and time; an engrafting date and time; an injecting date and time; an identified peak time for harvesting; a sample cell extracting days and the like.

Where appropriate, step 904B may be further subdivided into the steps:

removing at least a part of the egg shell of the fertilized egg, preferably at the widest side comprising the air pocket, thereby exposing at least part of the chorioallantoic membrane (CAM);

optionally, puncturing the chorioallantoic membrane (CAM) to enable the air pocket to shift to a desired location; and optionally, placing a tube into the chorioallantoic membrane (CAM). The placement of the tube may encourage blood vessels to grow around the tube.

Where appropriate, step 910B may further include the steps:

In step 912B—analyzing the harvested sample;

In step 914B—analyzing the imaging captured during the process, or captured at a given time/time duration;

In step 916B—analyzing the embryo.

It is noted that step 908B and step 910B may be repeated a plurality of times, for example, where a variety of types of exogenous material are to be applied. Thus, where required, a population of cells may be applied to the chorioallantoic membrane (CAM) of a fertilized egg and the fertilized egg then returned to the incubator for a period of time sufficient to allow engraftment of the implant to occur. The applicator may then be used to deliver another exogenous material such as a chemical or biological agent before again incubating the fertilized egg.

Figure 9C:
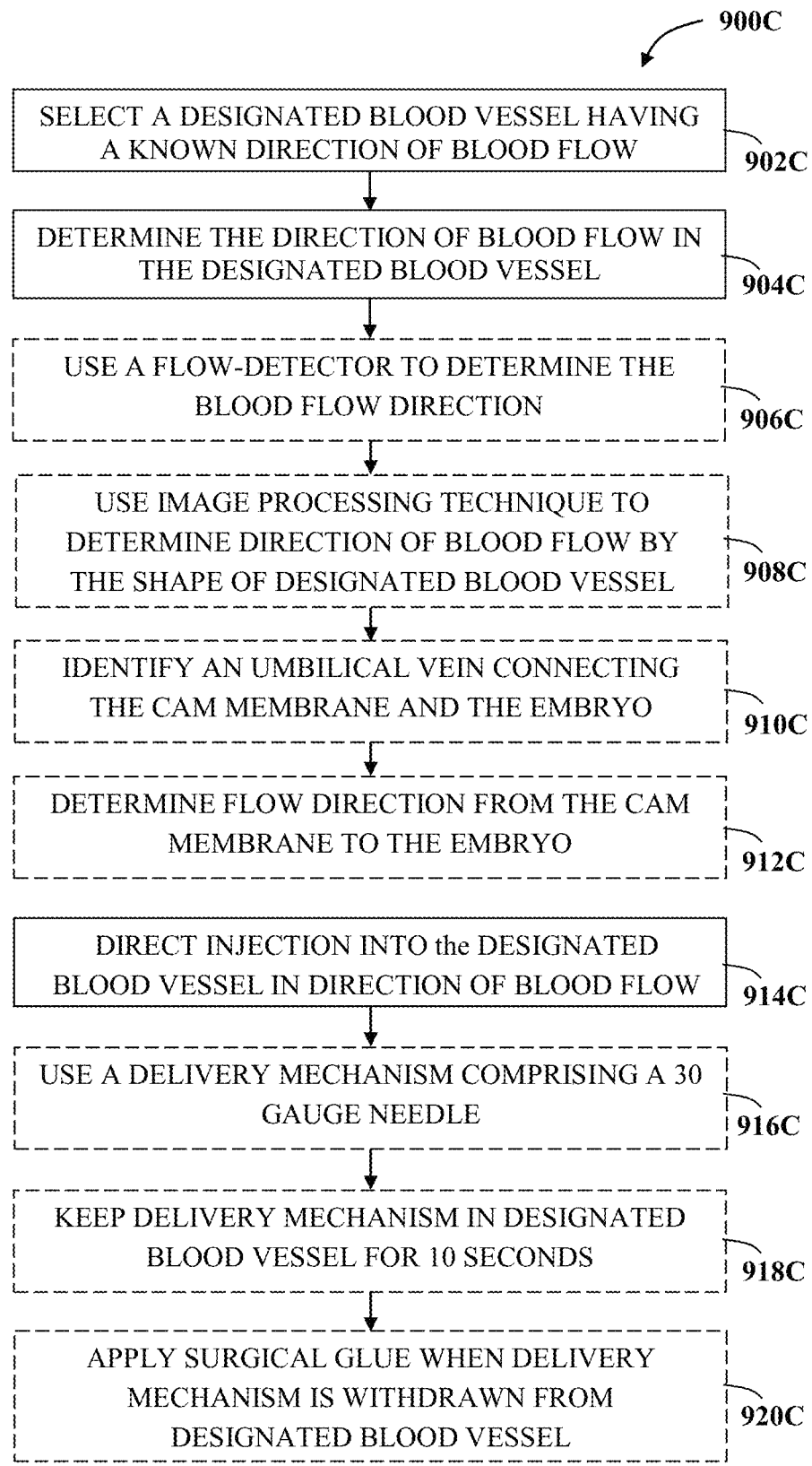
FIG. 9C is a flowchart representing a method of injecting for use with the automated system for the collection of biological samples.

Reference is now made to the flowchart of FIG. 9C, there is provided a possible method of injecting, which is generally indicated at 900C, for use with the automated system for the collection of biological samples.

As appropriate, directing the injection into the designated blood vessel in the direction of blood flow is required to make injection efficient.

Optionally, a flow-detector is used to determine the blood flow direction of the designated blood vessel.

Optionally, an image processing technique is used and is configured to determine the direction of blood flow according to the shape of the designated blood vessel.

Optionally, the system is operable to identify the umbilical vein connecting the chorioallantoic membrane (CAM) and the embryo of the embryonated egg, and further determine that the direction of blood flow in the umbilical vein is from the chorioallantoic membrane (CAM) to the embryo.

Optionally, the system is operable to inject the exogenous material effectively by using a delivery mechanism that comprises a 30 gauge needle. Alternatively the gauge of the needle may be selected from within the range 25-34, in still other embodiments, needles with gauges of 24 and below may be preferred.

Optionally, the system is operable to inject the exogenous material and is configured to keep the delivery mechanism in the designated blood vessel for 10 seconds.

Optionally, the system is operable to inject the exogenous material and is configured to apply surgical glue when the delivery mechanism is withdrawn from the designated blood vessel. As appropriate, the jacketed needle may be used such that the jacket releases the glue upon withdrawal.

The method 900C includes the steps:

In step 902C, selecting a designated blood vessel having a known direction of blood flow;

In step 904C, determining the direction of the blood flow in the designated blood vessel; and In step 906C, optionally using a flow-detector to determine the blood flow direction in the designated blood vessel;

In step 908C, optionally using image processing technique configured to determine the direction of blood flow in the designated blood vessel according to the shape of the designated blood vessel;

In step 910C, optionally an umbilical vein is identified connecting the chorioallantoic membrane (CAM) and the embryo; and further in step 912C, the flow direction of blood flow is determined to be from the chorioallantoic membrane (CAM) to the embryo.

In step 914C, directing the injection into the designated blood vessel in the direction of blood flow;

In step 916C, optionally using a delivery mechanism comprising a 30 gauge needle, rather than 29 gauge needle;

In step 918C, optionally keeping the delivery mechanism in the designated blood vessel for 10 seconds;

In step 920C, optionally applying surgical glue when the delivery mechanism is withdrawn from the designated blood vessel;

It is noted that the glue may be inserted into a jacketed needle, for example, before injecting, thus upon withdrawal of the delivery mechanism the glue is being released around the needle automatically.

Figure 9D:
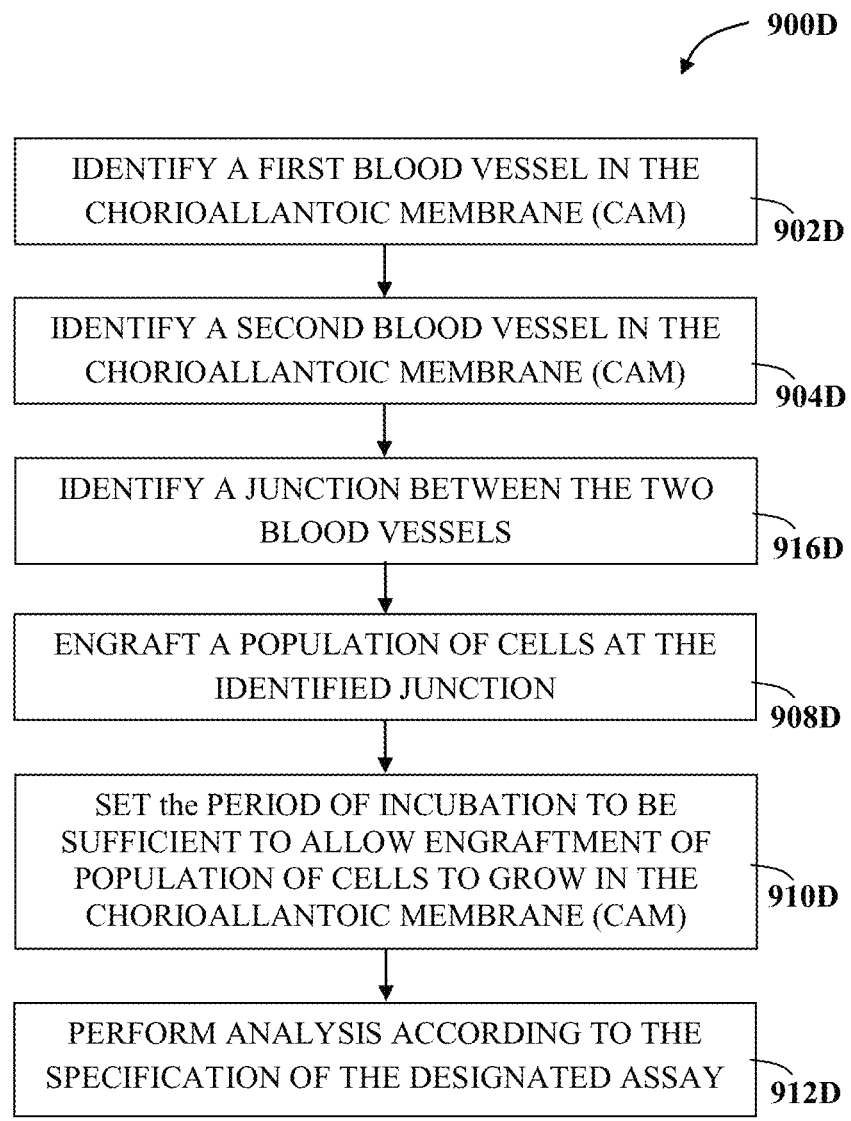
FIG. 9D is a flowchart representing a method of engrafting for use with the automated system for the collection of biological samples.

Reference is now made to the flowchart of FIG. 9D, there is provided a possible method of engrafting, which is generally indicated at 900D, for use with the automated system for the collection of biological samples.

As appropriate, following laboratory experiment, it has been explored that the junction between two blood vessels is more appropriate for engrafting. Thus, the process of engrafting the exogenous material comprises identifying a junction between a first blood vessel and a second blood vessel on the chorioallantroic membrane (CAM), and engrafting the population of cells at the junction.

It is noted that the selection of the appropriate junction for engrafting is not trivial and requires to know the blood vessel network of the chorioallantroic membrane (CAM) and other embryo associated organs to enable 'picking' the right location. Further, it is essential to know if a blood vessel is a vein or an artery, which is associated with the injection of the exogenous material, using an appropriate delivery mechanism, into the chorioallantroic membrane (CAM).

The method 900D includes the steps:

In step 902D, identifying a first blood vessel in the chorioallantoic membrane (CAM) of the fertilized egg;

In step 904D, identifying a second blood vessel in the chorioallantoic membrane (CAM) of the fertilized egg;

In step 906D, identifying a junction between the first blood vessel and the second blood vessel;

In step 908D, engrafting a population of cells at the identified junction of blood vessels;

In step 910D, setting the time period of incubation to be sufficient to allow engraftment of the population of cells to grow in the chorioallantoic membrane (CAM) of the fertilized egg; and In step 912D, performing analysis of the grown population of cells according to the specification of the designated assay associated with the fertilized egg.

Figure 9E:
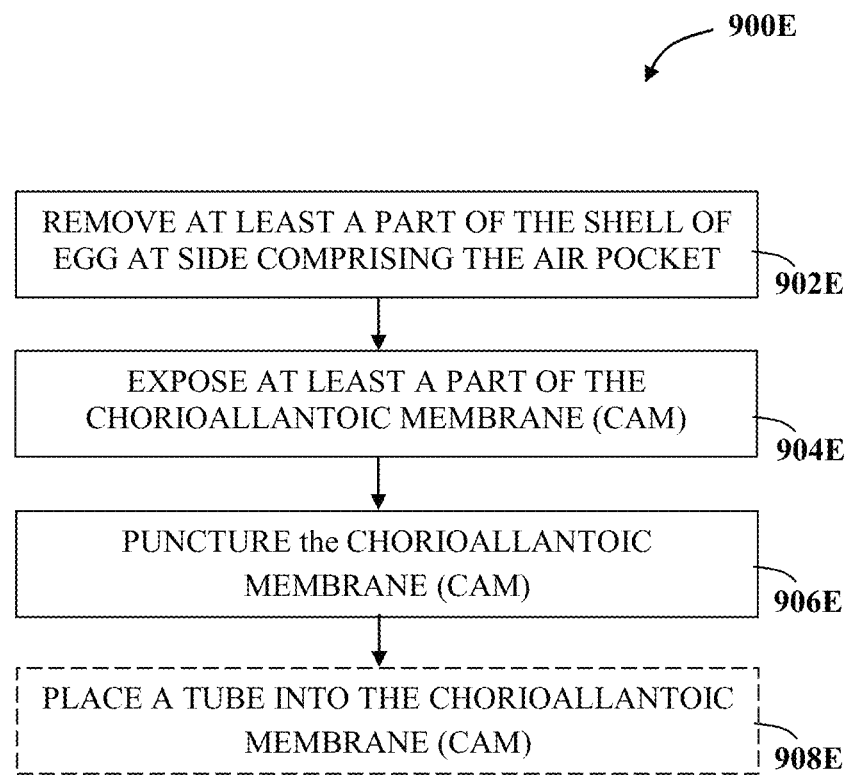
FIG. 9E is a flowchart representing a method of pricking for use with the automated system for the collection of biological samples.

Reference is now made to the flowchart of FIG. 9E, there is provided a possible method of pricking, which is generally indicated at 900E, for use with the automated system for the collection of biological samples.

Commonly, the automatic process of delivering is performed after the process of pricking, usually few days before. Alternatively, pricking may be performed on the same day prior to delivering the exogenous material.

Pricking the chorioallantroic membrane (CAM) of the at least one fertilized egg may be performed by the shell removal apparatus. The process of pricking may include removing at least a part of the egg shell of at the widest side comprising the air pocket and exposing the chorioallantoic membrane (CAM) to allow puncturing the chorioallantoic membrane (CAM) and further enable the air pocket to shift to a desired location. Additionally, a tube may be placed into the chorioallantoic membrane (CAM) to encourage blood vessels to grow around the tube and to ease the actions of engrafting and injecting. The tube end may be coated with pro-angiogenic material, or release an air flow containing a reduced or increased concentration of oxygen (15-30%). Alternating application of diverse oxygen concentrations may result in robust blood vessel growth, for example at E5 17% oxygen may induce hypoxia driving blood vessel proliferation, while following implanting of exogenous material, an increase in oxygenation may improve implanted cell vitality and release of growth stimulatory signals.

Thus, the method 900E includes the steps:

In step 902E, removing at least a part of the shell of the fertilized egg at the wide side which comprises the air pocket (FIG. 1A, item 70);

In step 904E, exposing at least a part of the chorioallantoic membrane (CAM) of the fertilized egg;

In step 906E, puncturing the chorioallantoic membrane (CAM) of the fertilized egg is performed to enable the air pocket to move to the highest point wherever the shell is pricked; and In step 908E, optionally a tube is placed into the chorioallantoic membrane (CAM) such that a designated blood vessel may be encouraged to grow around the tube. This may take several days, thus it is suggested to be applied at the time of pricking, few days before delivering.

It is further noted that the step of pricking is commonly performed on a different day before the delivering step (step 908A, FIG. 9A). Alternatively, it may be performed on the same day. Accordingly, when the chorioallantoic membrane (CAM) is punctured, some Amnium may be removed.

Figure 10:
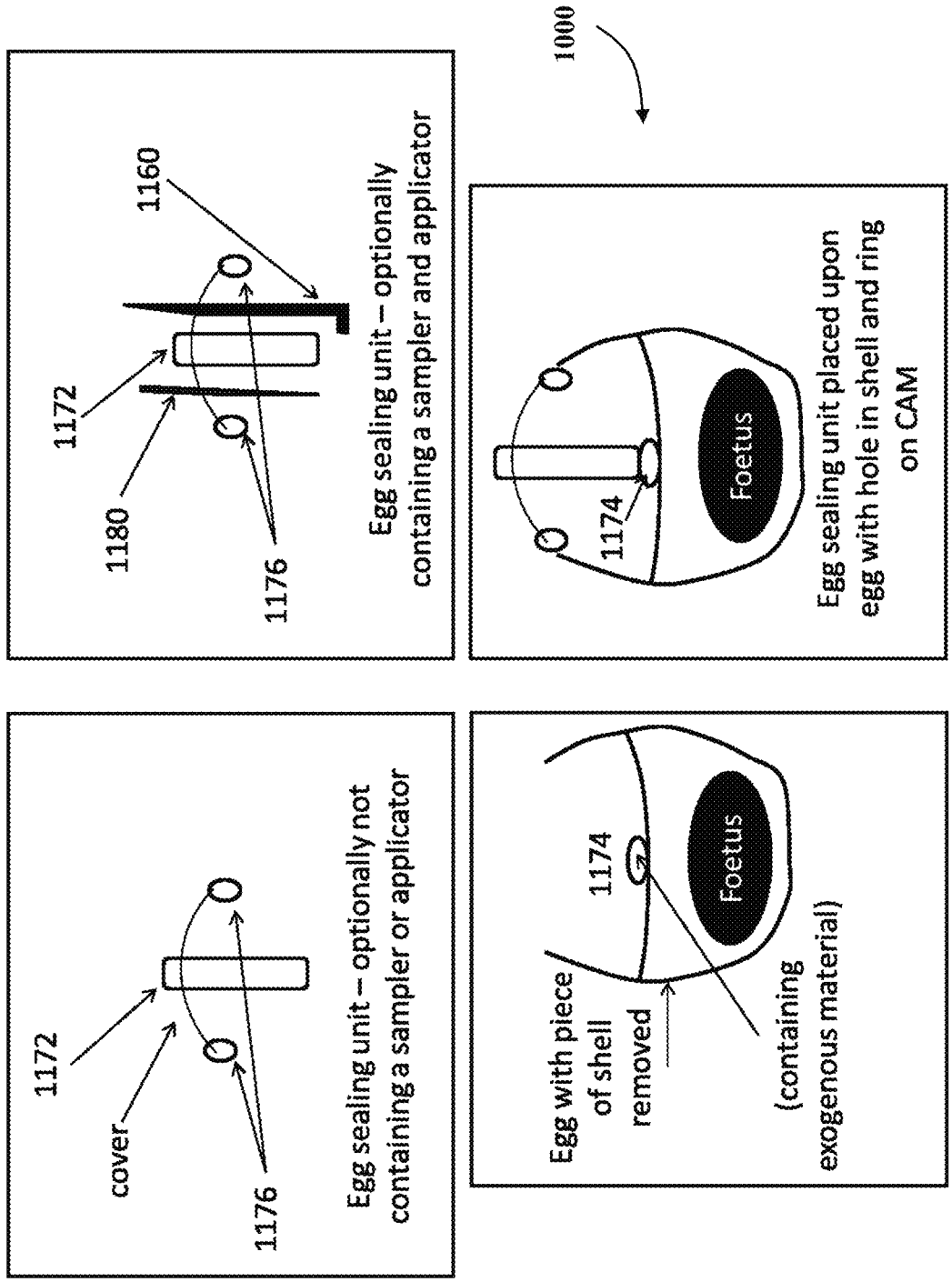
FIG. 10 schematically represents a possible embodiment of an egg sealing unit for use with the biological sample collection system.

Egg Sealing Unit:

Reference is now made to FIG. 10, in which there is provided an embodiment of an egg sealing unit, which is generally indicated at 1000, of the currently disclosed subject matter. The egg sealing unit diagram 1000 comprises a sampler 1160, an imaging adaptor 1170, and an applicator 1180.

The imaging adaptor 1170 may comprise a conduit 1172 for light traveling between the CAM and the egg shell surface, a ring 1174 and a seal 1176.

The conduit 1172 for light traveling between the CAM and the egg shell surface, may be used for transmitting lightwaves (emitted from a bright, fluorescent or laser light source, for example) and optionally includes a series of optical modifiers such as lenses and filters. At the end of the light conduit in proximity to the CAM, the light conduit 1172 may attach to a ring 1174 (plastic or silicone, for example) that is lying on the CAM, such that its light beam is focused on the CAM and xenografted material present within the confines of the ring 1174. At the end of the light conduit 1172 in proximity to the egg shell surface, the light conduit 1172 may attach to an imaging unit 1170. The light conduit 1172 is impermeable to water such that no condensation will form within, allowing constant unhampered imaging of the ring 1174 and its contents on the CAM.

The light conduit 1172 can be made of glass, or any suitable light transmitting material. Multiple light conduits may be incorporated into a single egg sealer unit 1000, such that multiple rings containing exogenous materials can be monitored within the same egg simultaneously.

The seal 1176 may comprise a gel, wax or other sealant sealing the egg shell opening to the light conduit 1172, such that no contamination can enter the egg, and that the interior of the egg does not dry out.

The ring 1174 may be placed on the CAM up to several days prior to implantation of the exogenous material, during this period the ring 1174 undergoes a form of binding with the CAM such that it cannot be moved without tearing the CAM, furthermore liquids and solids placed within the ring 1174 are confined to the ring area and do not leak under the ring 1174. The ring 1174 whereabouts is therefore a suitable indicator for determining the location of the exogenous material on the CAM, for example for placing the egg sealing unit 1000, or for directing the applicator 1180 or sampler 1160 or imager 1170.

The sampler 1160 may be incorporated into the egg sealing unit 1000, comprising the apparatus described in the Sampler section.

The applicator 1180 may be incorporated into the egg sealing unit 1000, comprising the apparatus described in the Applicator section.

In one example, multiple rings may be placed on the CAM, each having a different identifier (colour, number or name, for example), each containing a different exogenous material, such as cancer cells from different patients or sources. Thus, drug sensitive cells, tissues or organisms and drug resistant cells, tissues or organisms can be engrafted in the same egg and treated under equivalent intra-egg conditions with the same external modulators.

EXAMPLES

For illustrative purposes only, a selection of examples are presented below to demonstrate the usefulness of various embodiments of the automated biological sample collection system 200A (FIG. 2A):

Growth of Viruses for Generation, Testing or Development of Vaccines

Viruses may be produced in embryonated chick eggs after injection into the allantois, blood supply, yolk sac, or chorion. By using a biological sample collection system such as described hereinabove, the accuracy of the injection may be increased. This is particularly so when shell-less eggs are incubated. Furthermore, it is noted that the use of shell-less eggs also allows for rapid and accurate identification of dead embryos which may be readily removed.

Accordingly, eggs may be broken into individual compartments of the egg support apparatus, optionally this step may be performed by the shell-removal mechanism, although alternatively this step may be carried out manually. The eggs may be incubated to the appropriate age for the particular virus and administration route.

Once the embryos reach the appropriate age, the egg support apparatus may move the eggs to the applicator where, using machine vision, the appropriate portion of the egg (allantois, amniotic sac, yolk sac, blood vessel) may be identified, and injected robotically, for example, using an automated version of a syringe-holding device such as that described by Kelling and Schipper, 1976.

For example, the yolk or appropriate blood vessels may be identified by means of their color, shape, size or other chemical, physical or biological characteristics, and the syringe may thereby be guided towards them automatically. Although the allantois and amniotic sac may be more difficult to identify automatically, an automated algorithm may be generated in order to allow identification of such elements.

Alternatively, an operator using a video-link to the inside of the machine, may perform the initial positioning of the manipulator, to allow the injection to proceed automatically thereafter.

While still in the chamber, dead embryos, or those sufficiently growth-stunted to be likely to die may be readily identified and removed.

Assays of Chemotherapies on Human or Mammalian Cancer Cells Transplanted to the Egg A) Hematological Malignancies:

i) Patient Samples of Blood Cancer for Theranostics.

According to another application, blood cancer samples may be collected from individual patients for theranostics. A suspension of blood cancer cells taken from the peripheral blood or bone marrow of patients suffering from candidate conditions, such as leukemia, lymphoma, myeloma and the like, may be prepared for injecting into eggs.

Fertilized shell-less eggs may be prepared in individual compartments, either manually or using a shell removal apparatus. The shell-less eggs may be incubated to the appropriate age for each type of virus and administration route.

Upon the eggs reaching sufficient maturity, typically after 7-9 days of incubation for chicken eggs or 8-11 days for turkey eggs, the tray of the egg support mechanism may be moved to the applicator.

Using machine vision, appropriate blood vessels in the eggs may be identified, by color and size, for example. The manipulator may guide a syringe toward the blood vessels. The syringe would typically be filled with the prepared suspension of blood cancer cells with typically about 1-2 million cells being injected into each egg.

Following the application of cancerous cells, the tray of the egg support apparatus may be returned to the incubator for an additional 2-3 days during which the cancer may become engrafted.

Following the engraftment of the cancer, the applicator may be used to inject chemotherapeutic agents intravenously.

Following a third incubation period, the bone marrow or other other embryo tissues such as liver, spleen or the like, may be assayed, either manually or using the sampler, for the presence of human cancer cells. Variously, sampling may use the polymerase chain reaction (PCR) for human DNA, or human cell-surface markers by fluorescence aided cell sorting, or human cell death markers. Whole animal imaging may use cells made fluorescent in the infrared with lentiviral vectors driving expression of appropriate proteins such as Turbo635 (Evrogen).

ii) Blood Cell Lines for Drug Development.

Laboratory cancer cell lines may be obtained which are engineered to express far-red fluorescing proteins such as m-cherry, Turbo635 (Evrogen) or the like.

As above, fertilized shell-less eggs may be prepared in individual compartments, either manually or using a shell removal apparatus. The shell-less eggs may be incubated to the appropriate age for each type of virus and administration route.

Upon the eggs reaching sufficient maturity, typically after 7-9 days of incubation for chicken eggs or 8-11 days for turkey eggs, the tray of the egg support mechanism may be moved to the applicator.

Using machine vision, appropriate blood vessels in the eggs may be identified, by color and size, for example. The manipulator may guide a syringe toward the blood vessels. The syringe would typically be filled with the cancer cell lines of blood cancer cells with typically about 1-2 million cells being injected into each egg.

Following the application of cancerous cells, the tray of the egg support apparatus may be returned to the incubator for an additional 2-3 days during which the cancer may become engrafted.

Following the engraftment of the cancer, the applicator may be used to inject agents, such as chemotherapeutic agents and the like, intravenously.

Following a third incubation period, the sampler may use whole-body imaging with green exciting light to assay the killing of cancer cells by therapeutic agents.

Alternatively, non-engineered cells may be used, and cells tagged with magnetic nanoparticles such that the sampler may use MRI imaging.

B) Solid Cancers i) Patient Samples for Theranostics

Tumor tissue may be obtained from patients by removal during surgery or biopsy, for example. Tissue may be cut into 1 mm cubes using a Mcilwain tissue chopper, for example. Alternatively, tissue may be minced and suspended in a gel such as matrigel, and applied to the chorioallantoic membrane (CAM).

The biological sampling system may be utilized to prepare suitable host eggs, for example, using the methods described above.

The applicator may be used to place the tumor tissue cubes onto the chorioallantoic membrane (CAM) of E8 chicken embryos, for example. The eggs may be incubated again for about three days until engraftment of the tissue occurs.

Following the engraftment of the cancer, the applicator may be used to inject chemotherapeutic agents intravenously. Lipid soluble chemotherapeutic agents can be applied to the chorioallantoic membrane (CAM) without injection. Phototherapy activated-drugs (based on porphyrins) can also be used on CAM-grafted tumors. Typically, we have to calibrate route of drug administration for each chemical—water soluble drugs also can be dripped on the CAM. Where suitable, chemical agents may be formulated such that they can be dripped or placed on the CAM distal to the implanted exogenous material, such that they are absorbed by the underlying CAM blood vessels thereby entering the chick blood stream.

Following a third incubation period of, say, 3-5 days, grafted tumor pieces in treated and untreated embryos may be photographed, and their size compared. Thus candidate drugs may be compared for their effectiveness in reducing tumor growth.

ii) Cell Lines for Drug Development.

Laboratory cancer cell lines may be obtained which are engineered to express green fluorescent protein, for example. A suspension may be prepared of such cells in a gelling matrix material (e.g. matrigel or puramatrix).

The biological sampling system may be utilized to prepare suitable host eggs, for example, using the methods described above.

The applicator may be used to place the cell suspension upon the CAM of E8 chick embryos. The suspension may be contained upon the CAM within a plastic ring, for example. The eggs may be incubated again for about three days until engraftment of the tissue occurs.

Following the engraftment of the cancer, the applicator may be used to inject chemotherapeutic agents intravenously.

Following a third incubation period of, say, 3-5 days or so, grafted tumor pieces of the laboratory line cancer cells in treated and untreated embryos may be photographed, and their size compared. The vitality or metabolic profile of the cancer cells may be rapidly assessed through imaging of the reporter label (e.g., GFP fluorescence), or following tumor tissue processing, biomarkers can be analyzed (e.g., by immunohistochemistry, Western blot, flow cytometry, PCR, whole mount immunofluorescence. Thus candidate drugs may be compared for their effectiveness in reducing tumor growth, as well as their ability to reach the tumor in detectable concentrations.

iii) Metastasis Studies

The biological sampling system may be used to detect metastasis of applied cancer cells to the internal organs of an embryo, using whole-animal imaging techniques such as MRI, whole animal fluorescence imaging, or dissection and histological or FACS analysis, for example, as described above.

Assays for Angiogenic Properties of Substances Applied to the Chorioallantoic Membrane (CAM)

Preparations of angiogenic or anti-angiogenic solutions may be absorbed onto 1 cm radius pieces of filter paper, for example. The applicator of the biological sampling system described herein may be used to place such preparations onto the chorioallantoic membrane (CAM) of E5 embryos, for example.

Following an incubation period of about 2-7 days, the sampler may be used to measure the generation or reduction of blood vessels, for example, by using photography of the chorioallantoic membrane (CAM) and automated image analysis.

Assays of Toxicity to the Embryo (Teratogenicity), Transplanted Human or Mammalian Skin Transplanted to the CAM, Including Irritation, Sensitization etc.

i) Teratogenicity Testing

New compounds for use in industrial, medical, cosmetic or other industries would be injected intravascular as above, and embryos may be examined at E18 or earlier for morphological abnormalities.

ii) Dermatological Testing

Human skin, consisting of epidermis and a few millimeters of dermis may be obtained (i.e. from cosmetic surgery clinics), and cut into 6 mm rings with a dermal punch. The tissue may be placed dermis side down on the chorioallantoic membrane (CAM) of E6-9 eggs, and further incubated for two days until engraftment. Optionally, the chorioallantoic membrane (CAM) can be mildly abraded with lens tissue to cause bleeding and thereby improve engraftment of the skin. The cutting of the skin and the application of the samples may be performed automatically by the applicator or manually, as required.

Following engraftment, the skin may be treated with potential irritants or sensitizers, UV irradiated, treated with suntan lotion etc. and incubated for an additional time.

Following further incubation, the skin may be assayed by histology etc., using conventional methods. It is noted that the sampler may further assay the skin implant during the incubation process, or at the end of such process, using a non-invasive imaging system.

Additional dermatological applications may include testing for the introduction of material such as: viruses (herpes), genes (gene therapy), examination of transcutaneous absorption (by taking blood samples from the embryo), bacteria into the skin (acne) or the like and combinations thereof.

The scope of the disclosed subject matter is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

It should be appreciated to those skilled in the art that the invention may not be limited to the details of the foregoing illustrative embodiments and that the present invention may be use various other embodiments in other specific forms without departing from the nature or essential attributes thereof. The present embodiments are therefore to be considered in all respects as illustrative and not restrictive.

Those skilled in the art to which this invention pertains will readily appreciate that numerous changes, variations and modifications can be made without departing from the scope of the invention mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the disclosure.

What is claimed is:

1. An egg sealing unit for sealing an egg from which a section of shell has been removed, said egg sealing unit comprising:
    a cover;
    at least one sampler configured to collect samples from at least one fertilized egg;
    at least one applicator configured to deliver exogenous material to the fertilized egg; and
    at least one imaging adaptor providing a light conduit for light travelling between a chorioallantroic membrane (CAM) to a surface of the egg,
    wherein said imaging adaptor comprises an indication ring for indicating the location of exogenous material on the CAM.

2. The egg sealing unit of claim 1 wherein said egg sealing unit comprises a sealant configured to seal an egg shell opening.

3. The egg sealing unit of claim 1 wherein said sampler, applicator and imaging adaptor, are hermetically joined via sealant to the cover of the egg sealing unit.

4. The egg sealing unit of claim 1 wherein said imaging adaptor comprises a ring configured to bind to the CAM and preventing leakage of exogenous material located therewithin.

5. The egg sealing unit of claim 1 wherein said imaging adaptor comprises at least one light source.

6. The egg sealing unit of claim 1 wherein said imaging adaptor comprises light modifiers.

7. The egg sealing unit of claim 1 wherein said imaging adaptor comprises lenses configured to focus light onto the CAM.

8. The egg sealing unit of claim 1 wherein said light conduit is configured to attach to a ring lying upon the CAM.

9. The egg sealing unit of claim 1 wherein said light conduit extends from proximate to the CAM to proximate to the egg shell surface.

10. The egg sealing unit of claim 1 wherein said light conduit is impermeable such that no condensation forms therewithin.

11. The egg sealing unit of claim 1 comprising a plurality of light conduits each said light conduit focusing upon a separate ring containing exogenous material upon the CAM.

12. The egg sealing unit of claim 1 further comprising an imaging unit.

\* \* \* \* \*